United States Patent
Sanada et al.

(10) Patent No.: US 8,300,912 B2
(45) Date of Patent: Oct. 30, 2012

(54) CONTINUOUS X-RAY IMAGE SCREENING EXAMINATION DEVICE, PROGRAM, AND RECORDING MEDIUM

(75) Inventors: Shigeru Sanada, Kanazawa (JP); Rie Tanaka, Kanazawa (JP); Nobuo Okazaki, Tokyo (JP)

(73) Assignee: National University Corporation Kanazawa University, Ishikawa (JP)

( * ) Notice: Subject to any disclaimer, the term of this patent is extended or adjusted under 35 U.S.C. 154(b) by 1000 days.

(21) Appl. No.: 12/160,093

(22) PCT Filed: Jan. 5, 2007

(86) PCT No.: PCT/JP2007/050367
§ 371 (c)(1),
(2), (4) Date: Sep. 30, 2008

(87) PCT Pub. No.: WO2007/078012
PCT Pub. Date: Jul. 12, 2007

(65) Prior Publication Data
US 2009/0097731 A1    Apr. 16, 2009

(30) Foreign Application Priority Data

Jan. 5, 2006  (JP) ................................ 2006-000587
Jun. 22, 2006  (JP) ................................ 2006-172760

(51) Int. Cl.
*G06K 9/70*    (2006.01)
*G06K 9/78*    (2006.01)
*G06T 7/20*    (2006.01)
*G03N 23/12*    (2006.01)

(52) U.S. Cl. ........ 382/132; 382/130; 382/133; 382/134; 378/69; 378/901

(58) Field of Classification Search .................. 382/107, 382/128, 130, 133, 134, 168, 272, 307, 325; 378/62, 69, 91, 98, 98.8, 162, 210, 901
See application file for complete search history.

(56) References Cited

U.S. PATENT DOCUMENTS

| | | | |
|---|---|---|---|
| 4,611,340 A * | 9/1986 | Okazaki | 378/95 |
| 4,977,587 A | 12/1990 | Honda | |
| 5,450,464 A | 9/1995 | Sakakibara | |
| 2002/0102023 A1 * | 8/2002 | Yamauchi | 382/199 |

(Continued)

FOREIGN PATENT DOCUMENTS

JP        3-21228 A    1/1991

(Continued)

*Primary Examiner* — Anastasia Midkiff
(74) *Attorney, Agent, or Firm* — Dickstein Shapiro LLP

(57) ABSTRACT

Using nature that a pixel value in a lung of a chest X-ray moving image varies due to heart beat, the variation information on the pixel value is effectively used for diagnosis such as of a lung embolism or a heart disease, considering the variation information as lung blood flow information. A continuous X-ray image screening examination device receives a chest X-ray moving image from an X-ray detector and receives an electrocardiogram to become original information on a heart beat variation from an electrocardiogram recording apparatus. From the dynamic state of the heart wall measured by the electrocardiograph or the chest X-ray moving image, the heart dynamic state during the cardiac chamber systolic and diastolic phases is grasped, and information such as the variation of the pixel value of the chest X-ray moving image due to increase (lung blood flow increase) of the blood flow from the heart to the lung during the cardiac chamber systolic phase is generated.

20 Claims, 21 Drawing Sheets

U.S. PATENT DOCUMENTS

2006/0293579 A1* 12/2006 Schmitt et al. .............. 600/407
2007/0031018 A1*  2/2007 Camus et al. ............... 382/130

FOREIGN PATENT DOCUMENTS

| JP | 6-165035 | 6/1994 |
| JP | 6-237924 | 8/1994 |
| WO | WO 00/18299 A1 | 4/2000 |
| WO | WO 2004/093684 A1 | 11/2004 |
| WO | WO 2004093684 A1 * | 11/2004 |
| WO | WO 2005/073915 A2 | 8/2005 |

* cited by examiner

FIG. 18
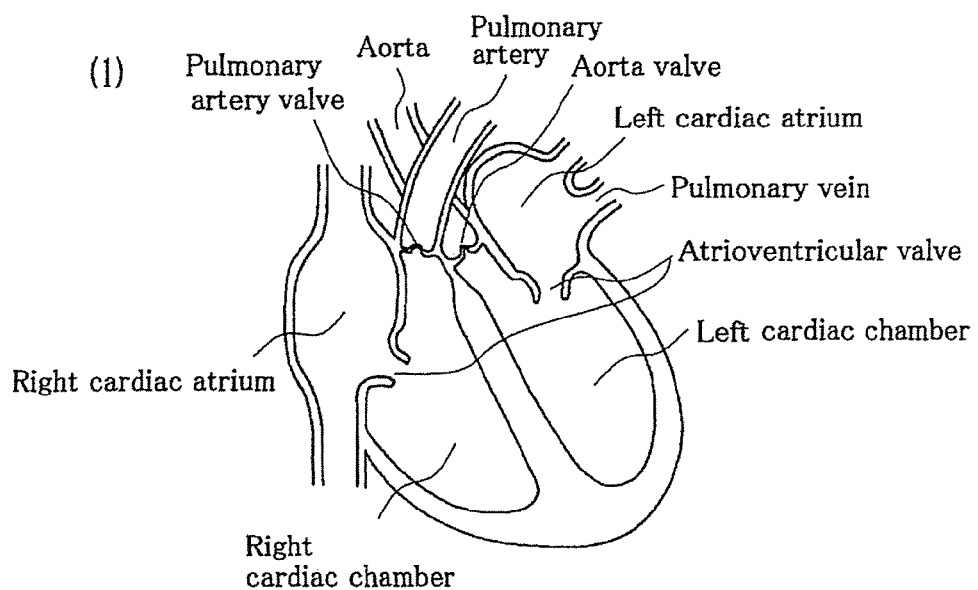
(1)
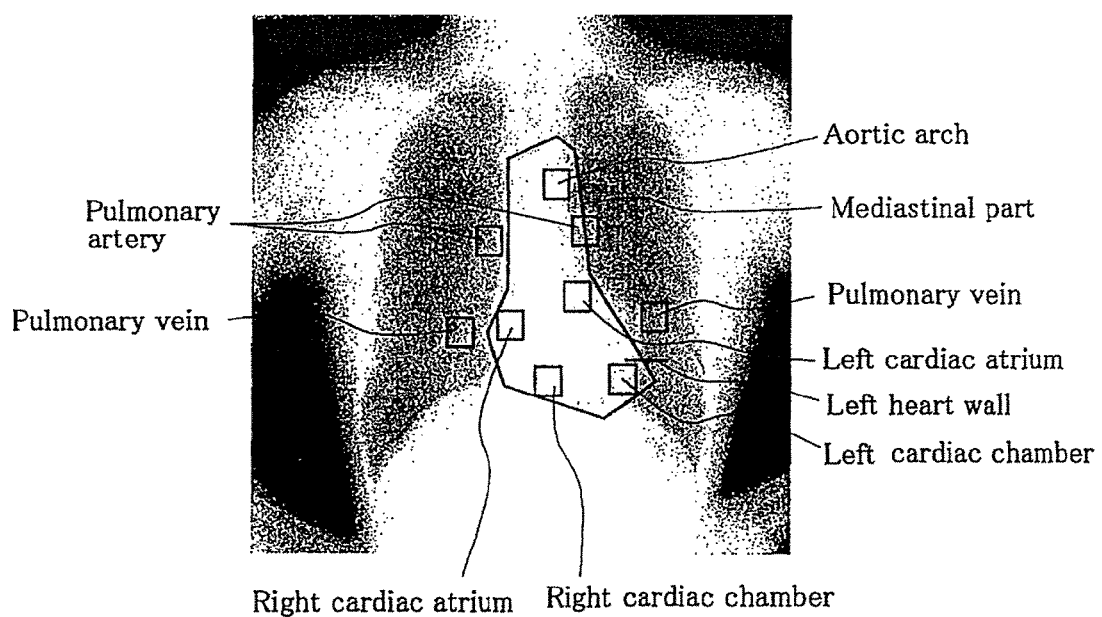
(2)

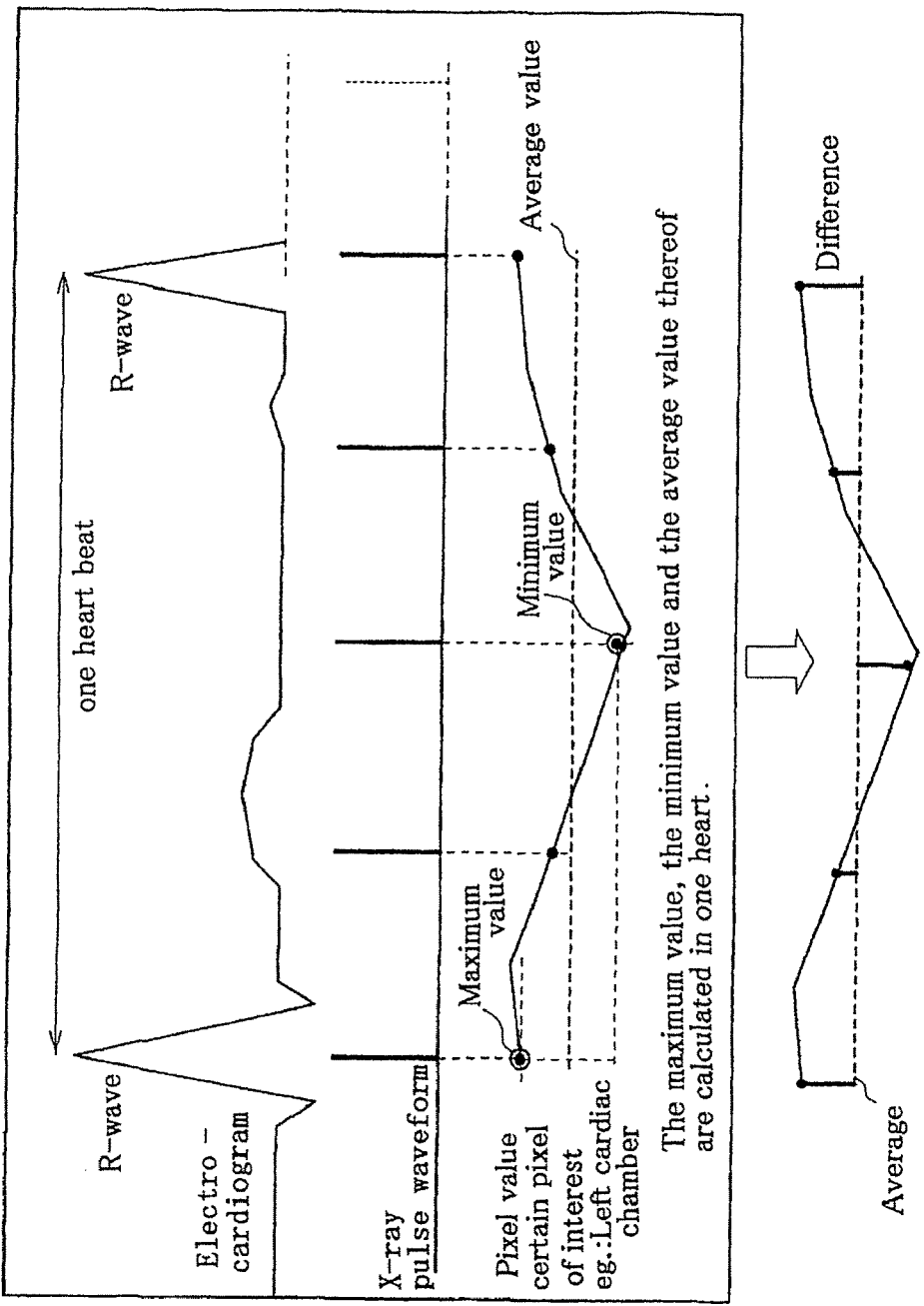

CONTINUOUS X-RAY IMAGE SCREENING EXAMINATION DEVICE, PROGRAM, AND RECORDING MEDIUM

CROSS REFERENCE OF RELATED APPLICATIONS

The present application demands for priority on Japanese Patent Application No. 2006-587 (applied on Jan. 5, 200) and Japanese Patent Application No. 2006-172760 (Jun. 22, 2006) and these applications are incorporated to the present specification with reference thereto.

TECHNICAL FIELD

The present invention relates to continuous X-ray image screening examination technology carrying out computer-analysis with an X-ray moving image and an electrocardiogram and generates information for assessing blood flow such as pulmonary blood flow and cardiac blood flow.

RELATED ART

In general, a lung embolism refers to a circulatory disorder caused by an embolus being carried on venous blood flow to close a pulmonary artery (a blood vessel transmitting venous blood for getting oxidized to the lung). For example, an economy-class syndrome being one of the lung embolism is a disease caused by maintaining the state of sitting on a seat with the same posture for a long time and, thereby, venous blood in the periphery of the rear side of a geniculum flow to form an embolus, which is a blood clot that results in a lung embolism. Such a lung embolism causes an embolus to close the pulmonary artery and will, therefore, give rise to abnormality in pulmonary blood flow.

In order to diagnose this a lung embolism, an electrocardiogram, blood examination, chest X-ray or cardiac ultrasonography and the like are carried out. Those examinations are useful as a differential diagnosis and a collateral evidence for the diagnosis. However, those examinations are not sufficient as the last evidence for a diagnosis of a lung embolism. Therefore, a pulmonary blood flow scintigraphic test or a pulmonary angiography examination is carried out.

The pulmonary blood flow scintigraphic test utilizes the nature of drug injected to a venous blood vessel gathered in the lung to detect X-ray emitted from the drug and thereby to create an image of the pulmonary blood flow. Specifically, a particle of a drug temporarily forms an embolus to stay in a capillary in the lung. The nature of the particle thereof getting defective in the case where no blood flow is present is utilized to obtain the distribution of the pulmonary blood flow. In addition, in the pulmonary angiography examination, a catheter is inserted and, thereafter, a contrast agent is injected in the right cardiac atrium, the left cardiac chamber and the pulmonary artery and the pulmonary blood flow is photographed with X-ray. Thereby, an image of the state of the pulmonary blood flow is created.

However, the pulmonary blood flow scintigraphic test and the pulmonary angiography examination require the use of intravenous injection and a catheter to inject a contrast agent. Therefore, an examinee has to have considerable strength for the examination. Therefore, a technique of imaging on the status of the pulmonary blood flow is demanded without burdening an examinee for the examination.

Computerized radiological technology with X-ray for imaging and quantitative measurement of the pulmonary blood flow and the like is being researched and developed. Computerized radiological technology with X-ray supplies an examinee with stable xenon, oxygen and helium which absorb X-ray and create an image of an affected area with X-ray for imaging and quantitative analyses on the affected area (see the Patent Document 1). In addition, technology of sustainably measuring pulmonary artery blood velocity with an ultrasonic echo sensor allowing all time observation on the pulmonary artery for sensing a decrease in the relevant velocity and thereby warn of the presence of a blood clot of the pulmonary artery or the embolus is disclosed (see Patent Document 2).

However, the technology in the Patent Document 1 requires supplying stable xenon and the like, which operate to absorb X-ray, to an examinee and, therefore, is not simple and convenient for realizing imaging of an affected area and, moreover, the burden on the examinee is significant, giving rise to a problem. In addition, the technology in the Patent Document 2 only uses the ultrasonic echo sensor and, therefore, cannot obtain sufficient information for a diagnosis on a blood clot in the pulmonary artery and the like.

Patent Document 1: Japanese Patent Application Laid-Open No. 5-279268
Patent Document 2: Japanese Patent Application Laid-Open No. 2003-235846

DISCLOSURE OF THE INVENTION

Therefore, the present invention is attained in view of such a circumstance and an object thereof is to provide a continuous X-ray image screening examination device, program and recording medium which do not impose a considerable burden on an examinee in an examination such as of a lung embolism or a heart disease causing abnormality in blood flow such as pulmonary blood flow and cardiac blood flow and allows simple and convenient generation of information effectively utilizable for a diagnosis on these diseases.

A continuous X-ray image screening examination device according to the present invention is a continuous X-ray image screening examination device to which an X-ray moving image of an examinee is input and which generates information for assessing blood flow with the X-ray moving image, characterized by comprising an image store storing a plurality of frames configuring the above described X-ray moving image and an analysis part reading a frame from the image store, calculating a pixel value within a predetermined range for each of the read frames and generating temporal variation of the calculated pixel value reflecting a heart beat variation as blood flow information.

In addition, the above described analysis part preferably reads a frame from the image store to generate blood flow information on temporal relation to the heart beat phase based on the read frame.

In addition, the continuous X-ray image screening examination device according to the present invention further comprises an electrocardiogram store where an electrocardiogram of the examinee is stored, characterized in that the above described analysis part reads the frame from the image store and the electrocardiogram from the electrocardiogram store respectively to generate blood flow information on temporal relation to the electrocardiogram based on the read frame.

In that case, the above described analysis part preferably has local pulmonary blood flow analyzing means for reading a plurality of frames from the image store and an electrocardiogram from the electrocardiogram store respectively, calculating an average pixel value of any region among a lung field region, a lung field region subjected to dividing and a region of interest designated by an operator for each of the read frame and generating an average pixel value for each of the regions and the above described read electrocardiogram as chronologically synchronized information.

In addition, the above described analysis part preferably has local cardiac blood flow analyzing means for reading a plurality of frames from the image store and an electrocardiogram from the electrocardiogram store respectively and calculating an average pixel value of a predetermined region inside a mediastinal part for each of the read frames.

In addition, the above described local pulmonary blood flow analyzing means preferably recognizes one hart beat from the above described electrocardiogram, calculates a rate of change of pixel from the average pixel value of each frame for one heart beat and compares the calculated rate of change of pixel for each of the above described regions.

In addition, the above described local pulmonary blood flow analyzing means preferably calculates, further, at least one among delay time since an R wave occurs in the above described electrocardiogram until the average pixel value is minimized, an angle of rising at and after a time point to minimize the average pixel value and the difference between the maximum value and the minimum value of the average pixel value.

In addition, the above described analysis part further has heart wall movement analyzing means for detecting a boundary site between the lung field region and the heart based on the pixel value for each frame to calculate a quantity of variation of the boundary site as heart wall movement.

In addition, the above described analysis part preferably has, further, pulmonary blood flow dynamic state analyzing means for reading a plurality of frames from the above described image store and the electrocardiogram from the electrocardiogram store respectively, specifying, from the electrocardiogram, timing when an R wave occurs, specifying a frame corresponding to the R wave, calculating the difference between pixel values of the specified frame and another frame for one heart beat and generating an image of a pulmonary blood flow dynamic state with the difference of the pixel values.

In addition, the above described analysis part preferably has, further, pulmonary blood flow dynamic state analyzing means for reading a plurality of frames from the above described image store and the electrocardiogram from the electrocardiogram store respectively, calculating the difference between pixel values of the temporarily adjacent frames and generating an image of pulmonary blood flow dynamic state with the difference of the pixel values.

In addition, the above described analysis part preferably has, further, pulmonary blood flow dynamic state analyzing means for reading a plurality of frames from the above described image store and the electrocardiogram from the an electrocardiogram store respectively, calculating an average value from the maximum value and the minimum value of pixel values of each frame for one heart beat for each pixel based on the electrocardiogram, calculating the difference between the above described pixel value and the calculated average value and generating an image of pulmonary blood flow dynamic state with the difference of the pixel values.

In addition, the above described analysis part preferably has, further, pulmonary blood flow distribution analyzing means for reading a plurality of frames from the above described image store and the electrocardiogram from the an electrocardiogram store respectively, specifying, from the electrocardiogram, timing when an R wave occurs, specifying a frame corresponding to the R wave, generating an MIP image for one heart beat, calculating the difference between pixel values of the MIP image and the image of the above described specified frame and generating an image of the pulmonary blood flow distribution with the difference of the pixel values.

In addition, the continuous X-ray image screening examination device further comprises a pulse waveform store storing an X-ray pulse waveform specifying timing for detecting X-ray, characterized in that the pulmonary blood flow dynamic state analyzing means reads an X-ray pulse waveform from the above described pulse waveform store to specify a frame corresponding to an R wave based on the X-ray pulse waveform.

In addition, the above described analysis part preferably calculates a pixel value of a lung region of the read frame, determines a frame corresponding to an R wave in the heart beat phase based on the pixel value and generates pulmonary blood flow information.

In addition, the above described analysis part preferably calculates heart wall movement from the read frame, determines a frame corresponding to an R wave in the heart beat phase based on the heart wall movement and generates pulmonary blood flow information.

In addition, the above described analysis part further has cardiac blood flow dynamic state analyzing means for reading a plurality of frames from the above described image store and an electrocardiogram from the electrocardiogram store respectively, specifying, from the electrocardiogram, timing when an R wave occurs, specifying a frame corresponding to the R wave, calculating the difference between pixel values of the specified frame and another frame for one heart beat and generating an image of cardiac blood flow dynamic state with the difference of the pixel values and cardiac blood flow distribution analyzing means for reading a plurality of frames from the above described image store and an electrocardiogram from the electrocardiogram store respectively, specifying, from the electrocardiogram, timing when an R wave occurs, specifying a frame corresponding to the R wave, generating an MIP image for one heart beat, calculating the difference between pixel values of the MIP image and the image of the above described specified frame and generating an image of the cardiac blood flow distribution with the difference of the pixel values, characterized in that the local cardiac blood flow analyzing means further recognizes one heart beat from the above described electrocardiogram, calculates a rate of change of pixel from the average pixel value of each frame for one heart beat and compares the calculated rate of change of pixel for each of the above described regions.

In addition, a continuous X-ray image screening examination program according to the present invention is a continuous X-ray image screening examination program using an apparatus comprising an image store storing a plurality of frames configuring an X-ray moving image of an examinee to generate information for assessing pulmonary blood flow with the above described X-ray moving image, characterized by causing a computer configuring the above described apparatus to execute a process (1) for reading a frame from the above described image store, a process (2) for calculating a pixel value within a predetermined range for each of the read frames and a process (3) for generating temporal variation of the calculated pixel value reflecting a heart beat variation as pulmonary blood flow information.

In addition, instead of the above described processes (2) and (3), a process (2)' for assuming the heart beat phase based on the above described read frame and a process (3)' for generating pulmonary blood flow information from the assumed heart beat phase and the above described read frame are preferably executed.

In addition, a computer configuring an apparatus comprising an electrocardiogram store storing an electrocardiogram of an examinee is preferably caused to execute a process (4) for reading an electrocardiogram from the above described electrocardiogram store, a process (5) for assuming the heart beat phase based on the read electrocardiogram and a process (6) for generating pulmonary blood flow information from the assumed heart beat phase and the above described read frame.

Without imposing a considerable burden on an examinee in examination such as of a lung embolism or a heart disease causing abnormality in blood flow such as pulmonary blood flow and cardiac blood flow, the present invention will enable simple and convenient generation of information effectively utilizable for a diagnosis on these diseases.

BRIEF DESCRIPTION OF THE DRAWINGS

FIGS. 18(1) and 18(2) are diagrams illustrating a mediastinal part analyzed by local cardiac blood flow analyzing means;

FIG. 21 illustrates another computer algorithm for producing images of a pulmonary blood flow dynamic state with the pulmonary blood flow dynamic state analyzing means 43.

Figure 1:
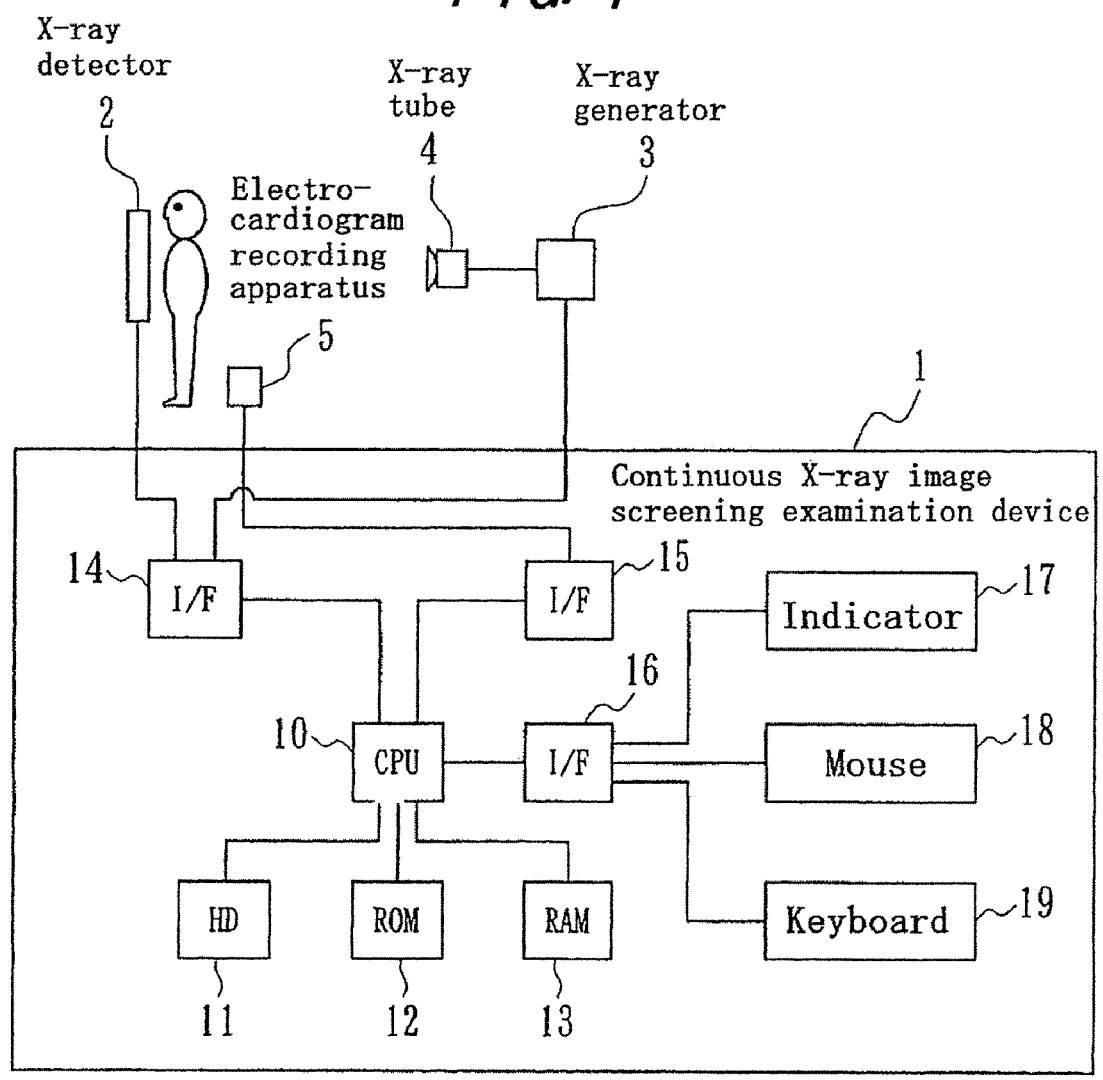
FIG. 1 is a schematic diagram illustrating a configuration of an entire system including a continuous X-ray image screening examination device 1 according an embodiment of the present invention.

DESCRIPTION OF THE SYMBOLS 1 continuous X-ray image screening examination device
2 X-ray detector
3 X-ray generator
4 X-ray tube
5 an electrocardiogram recording apparatus
10 CPU
11 HD
12 ROM
13 RAM
14, 15, 16 I/F
17 an indicator
18 mouse
19 keyboard
21 chest X-ray moving image store
22 X-ray pulse waveform store
23 electrocardiogram store
30 control part
40 analysis part
41 local pulmonary blood flow analyzing means
42 heart wall movement analyzing means
43 pulmonary blood flow dynamic state analyzing means
44 pulmonary blood flow distribution analyzing means

BEST MODE FOR CARRYING OUT THE INVENTION

An embodiment of the present invention will be described below in detail with the drawings.

[Summary of the Present Invention]

At first, the summary of the present invention will be described. The present invention uses the nature that the pixel value in a lung and a mediastinal part of a chest X-ray moving image varies due to heart beat. That is, focusing attention on the pixel value which increases and decreases according to blood flow such as pulmonary blood flow and cardiac blood flow due to heart beat, the variation information on the pixel value is effectively used for diagnosis such as of a lung embolism or a heart disease, considering this variation information of the pixel as information on blood flow such as pulmonary blood flow and cardiac blood flow. A chest X-ray moving image can be obtained from an X-ray detector and phase information on heart beat can be obtained from an electrocardiogram recording apparatus. In addition, the heart dynamic state during the cardiac chamber systolic and diastolic phases is grasped by an electrocardiogram. Therefore, with increase of the blood flow (blood flow increase of blood flow such as pulmonary blood flow and cardiac blood flow) from the heart to the lung during the cardiac chamber systolic phase, information such as the variation of the pixel value of the chest X-ray moving image due to increase of the relevant blood flow such as pulmonary blood flow and cardiac blood flow can be obtained highly accurately. The heart beat phase can be assumed from the pixel value or the dynamic state of the heart wall. Accordingly, heart beat phase information assumed from the pixel value or the dynamic state of the heart wall can also be used instead of the electrocardiogram to obtain the target information on blood flow such as pulmonary blood flow and cardiac blood flow. Details will be described later.

Figure 15:
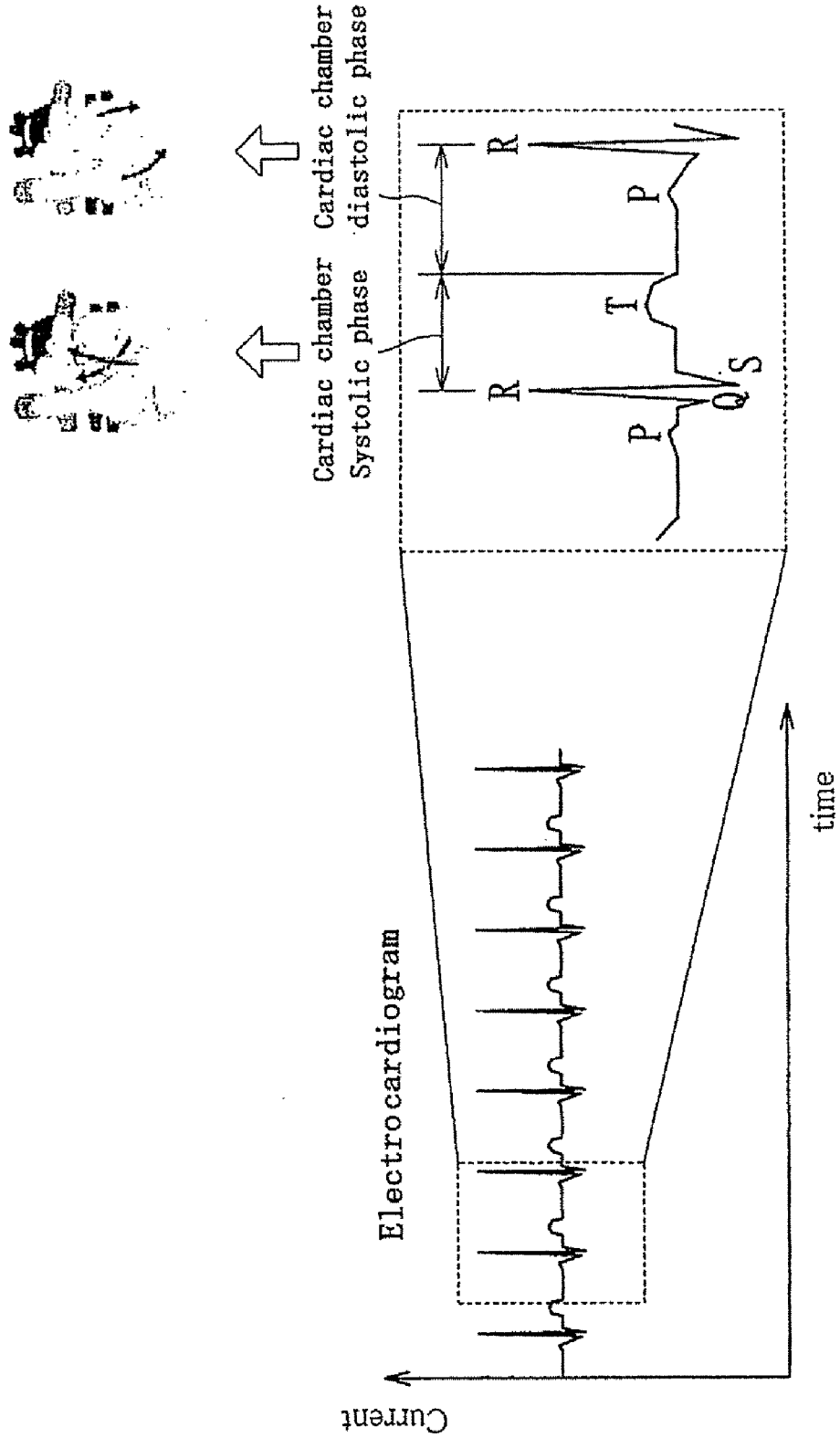
FIG. 15 illustrates diagrams for describing an electrocardiogram.

FIG. 15 illustrates diagrams for describing an electrocardiogram. In the drawing, the axis of ordinates represents heart beat current. The axis of abscissae represents time. This electrocardiogram is a curb for recording variation of faint action current (heart beat current) due to activities of cardiac muscles in a specific site on the body surface and follows the dynamic state of the heart. In the drawing, waveform portions (R waves) protruding upward appear periodically. This period corresponds to heart beats. One heart beat consists of an R wave, an S wave, a T wave, a P wave and a Q wave. An electrocardiogram will become a curb configured by repeating those waves temporarily in a continuous manner. A cardiac chamber systolic phase refers to a period up to the R wave, the S wave and the T wave, and blood flows from the heart to the lung. A cardiac chamber diastolic phase refers to a period after the T wave to the P wave and the Q wave, when blood flows from the lung to the heart.

In the cardiac chamber systolic phase illustrated in FIG. 15, blood flows from the heart to the lung pulmonary blood flow increases). Then the pixel value in the lung field region in the chest X-ray moving image increases. The reason hereof is that X-ray will hardly get likely to transmit due to presence of the pulmonary blood flow to decrease its transmissivity. With P being the pixel value and N being an X-ray amount detected by an X-ray detector (amount of incident ray to the X-ray detector), the following relation will be established. Likewise relation is established in the case of the cardiac blood flow.

$$P \propto 1/\log N \qquad (1)$$

The present invention focuses attention to such a nature. Its characteristic is to assess blood flow such as pulmonary blood flow in a pulmonary site and cardiac blood flow in a mediastinal site by quantitizing the pixel value of the chest X-ray moving image reflecting a heart beat variation and, thereby, effectively use the relevant quantitized information for diagnosis such as of a lung embolism or a heart disease. Thereby, for example, a site, where the pixel value increase less than another pulmonary site or a mediastinal site, can be determined and can be used as useful information for diagnosis such as of a lung embolism.

[Configuration]

FIG. 1 is a schematic diagram illustrating a configuration of an entire system including a continuous X-ray image screening examination device 1 according an embodiment of the present invention. This system is configured by a continuous X-ray image screening examination device 1, an X-ray detector 2, an X-ray generator 3, an X-ray tube 4 and an electrocardiogram recording apparatus 5. The internal configuration of the continuous X-ray image screening examination device 1 illustrates hardware resources. The continuous X-ray image screening examination device 1 comprises a CPU 10 executing respective processing according to a program, an HD 11 storing programs and data for executing respective processing, a chest X-ray moving image, an X-ray pulse waveform and an electrocardiogram, a ROM 12 storing system programs such as an OS and system data, a RAM 13 temporarily storing programs, data and the like, an I/F 14 relaying inputs and outputs of information with the X-ray detector 2 and the X-ray generator 3, an I/F 15 relaying inputs and outputs of information with the electrocardiogram recording apparatus 5, an indicator 17 displaying a chest X-ray moving image, an X-ray pulse waveform, an electrocardiogram, an analysis result and the like on a screen, a mouse 18 inputting operations of an operator, a keyboard 19 and an I/F 16 relaying the indicator 17 and the like.

The CPU 10 outputs a timing signal for the X-ray tube 4 to irradiate X-ray to the X-ray generator 3 through the I/F 14, inputs a chest X-ray moving image from the X-ray detector 2 through the I/F 14 to store in the HD 11. When the I/F 14 input X-ray information from the X-ray detector 2 to generate an X-ray pulse waveform, the CPU 10 inputs the relevant X-ray pulse waveform to store in the HD 11. The CPU 10 inputs an electrocardiogram from the electrocardiogram recording apparatus 5 through the I/F 15 to store in the HD 11. The CPU 10 reads programs and data for executing respective processing from the HD 11 or the ROM 12 to store in the RAM 13. And, according to the programs stored in the RAM 13, an operator operates the mouse 18 and the keyboard 19 to control the X-ray detector 2 and the X-ray generator 3 through the I/F 14. A chest X-ray moving image and the like are read from the HD 11 to execute respective analysis processing. The chest X-ray moving image, an analysis result thereof and the like are displayed in the indicator 17 through the I/F 16.

The X-ray detector 2 detects X-ray and, thereby, generates a chest X-ray moving image and X-ray information and output the relevant chest X-ray moving image and X-ray information to the continuous X-ray image screening examination device. For example, an examinee undergoes five-second examination and, then, the X-ray detector 2 generates 30 frames of chest X-ray moving images in five seconds and generates X-ray information so that the I/F 14 of the continuous X-ray image screening examination device generates an X-ray pulse waveform consisting of 30 units of pulse. This X-ray detector 2 is an appliance for converting the X-ray into an electrical signal to obtain an image and is an image pickup appliance with a planar detector which directly digitalizes the image. For example, an FPD (Flat Panel Detector) is used and since the FPD is highly sensitive to the X-ray, has wide image pickup vision and the image including no distortion compared with a fluoroscope such as a conventional I.I.—X-ray TV system, a clear and stable moving image can be obtained.

The examinee can undergo four-second examination and, then the X-ray detector 2 generates 24 frames of a chest X-ray moving image in four seconds to generate required X-ray information so that the I/F 14 of the continuous X-ray image screening examination device 1 generates an X-ray pulse waveform consisting of 24 pulses. In this case, using an oscilloscope displaying waveforms for four seconds on one screen is advantageous since the above described X-ray pulse waveforms can be displayed on one screen.

The X-ray generator 3 receives a timing signal from the continuous X-ray image screening examination device 1 to cause the X-ray tube 4 to irradiate X-ray at the relevant timing. With irradiation of X-ray by this timing signal, the X-ray detector 2 generates a chest X-ray moving image. The electrocardiogram recording apparatus 5 records an electrocardiogram during the above described five-second examination and outputs the relevant electrocardiogram to the continuous X-ray image screening examination device 1.

Here, the chest X-ray moving image generated by the X-ray detector 2, the X-ray pulse waveform generated by the I/F 14 of the continuous X-ray image screening examination device 1, the timing signal output to the X-ray generator 3 and the electrocardiogram generated by the electrocardiogram recording apparatus 5 are respectively brought into synchronization. Accordingly, the chest X-ray moving image, the X-ray pulse waveform and the electrocardiogram are stored together with the synchronized temporal information in the HD 11.

Figure 2:
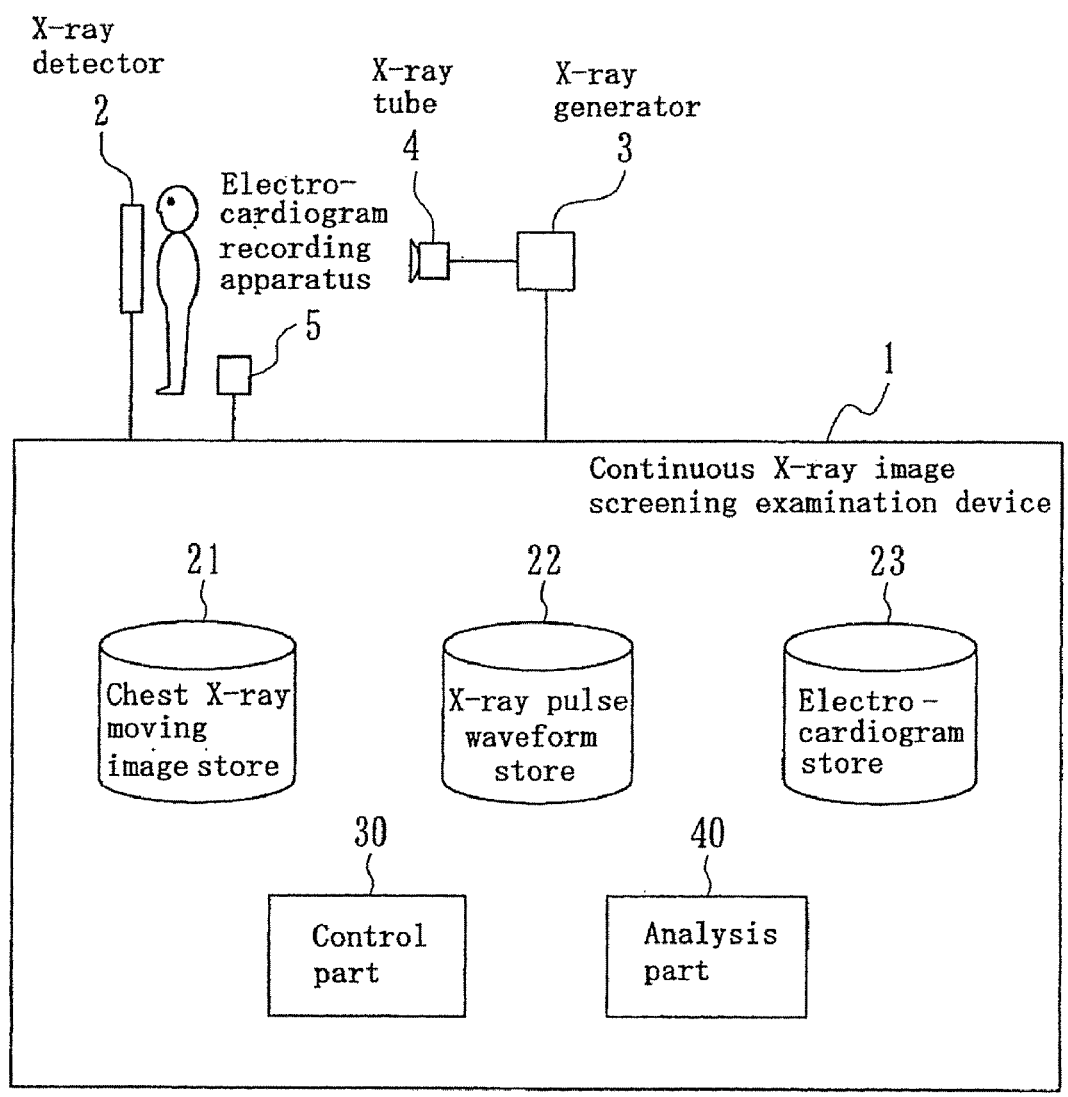
FIG. 2 is a block diagram illustrating a configuration of functions of the continuous X-ray image screening examination device 1.

FIG. 2 is a block diagram illustrating a configuration of functions of the continuous X-ray image screening examination device 1 illustrated in FIG. 1. This continuous X-ray image screening examination device 1 comprises a chest X-ray moving image store 21, an X-ray pulse waveform store 22, an electrocardiogram store 23, a control part 30 and an analysis part 40. The chest X-ray moving images generated by the above described X-ray detector 2 are stored in the chest X-ray moving image store 21. The chest X-ray moving image is stored for each of the examinees with 30 frames of image of the five-second examination as one set. Here, the chest X-ray moving image does not necessarily have to make one set with 5 seconds/30 frames but any chronological images generated in small interval will work. The X-ray pulse waveforms generated by the above described I/F 14 are also stored in the X-ray pulse waveform store 22. The X-ray pulse waveform includes 30 pulses in a five-second examination and is stored for each of examinees. An electrocardiogram recorded by the above described electrocardiogram recording apparatus 5 is stored in the electrocardiogram store 23. The electrocardiogram is a cardiac dynamic state waveform in a five-second examination and is stored for each of examinees.

The chest X-ray moving image stored in the chest X-ray moving image store 21, the X-ray pulse waveform stored in the X-ray pulse waveform store 22, the electrocardiogram stored in the electrocardiogram store 23 are synchronized information as described above. The chest X-ray moving image store 21, the X-ray pulse waveform store 22 and the electrocardiogram store 23 correspond to the HD 11 illustrated in FIG. 1.

The control part 30 starts an examination of an examinee by an operation of an operator. Specifically, the X-ray detector 2 is caused to generate the chest X-ray moving image; the I/F 14 is caused to generate an X-ray pulse waveform respectively. The electrocardiogram recording-apparatus 5 is caused to record an electrocardiogram. In that case, to the X-ray generator 3, the control part 30 outputs a timing signal for causing the X-ray tube 4 to irradiate X-ray. Here, in the case of generating 30 frames of the chest X-ray moving image in a five-second examination, a timing signal is output every 166 msec. When the examination of an examinee is completed, the control part 30 receives the chest X-ray moving image being an examination result from the X-ray detector 2 to store it in the chest X-ray moving image store 21. The X-ray pulse waveform is input from the I/F 14 and stored in the X-ray pulse waveform store 22. In the case where 30 frames of chest X-ray moving image is generated in the five-second examination, the X-ray pulse waveform will become pulse occurring every 166 msec. Moreover, the control part 30 receives an electrocardiogram from the electrocardiogram recording apparatus 5 to store it in the electrocardiogram store 23. Thus, the control part 30 stores the chest X-ray moving image, the X-ray pulse waveform and the electrocardiogram in the chest X-ray moving image store 21, the X-ray pulse waveform store 22 and the electrocardiogram store 23 respectively for each of the examinee.

The analysis part 40 reads, the chest X-ray moving image from the chest X-ray moving image store 21, the X-ray pulse waveform from the X-ray pulse waveform store 22 and the electrocardiogram from the electrocardiogram store 23 respectively for each of the designated examinees by operations of the operator and quantitized the pixel value of the chest X-ray moving image reflecting a heart beat variation based on the synchronized information hereof to display it on a screen. Thereby, pulmonary blood flow in a pulmonary site is assessed and will be used effectively for diagnosis such as of a lung embolism or a heart disease.

Figure 3:
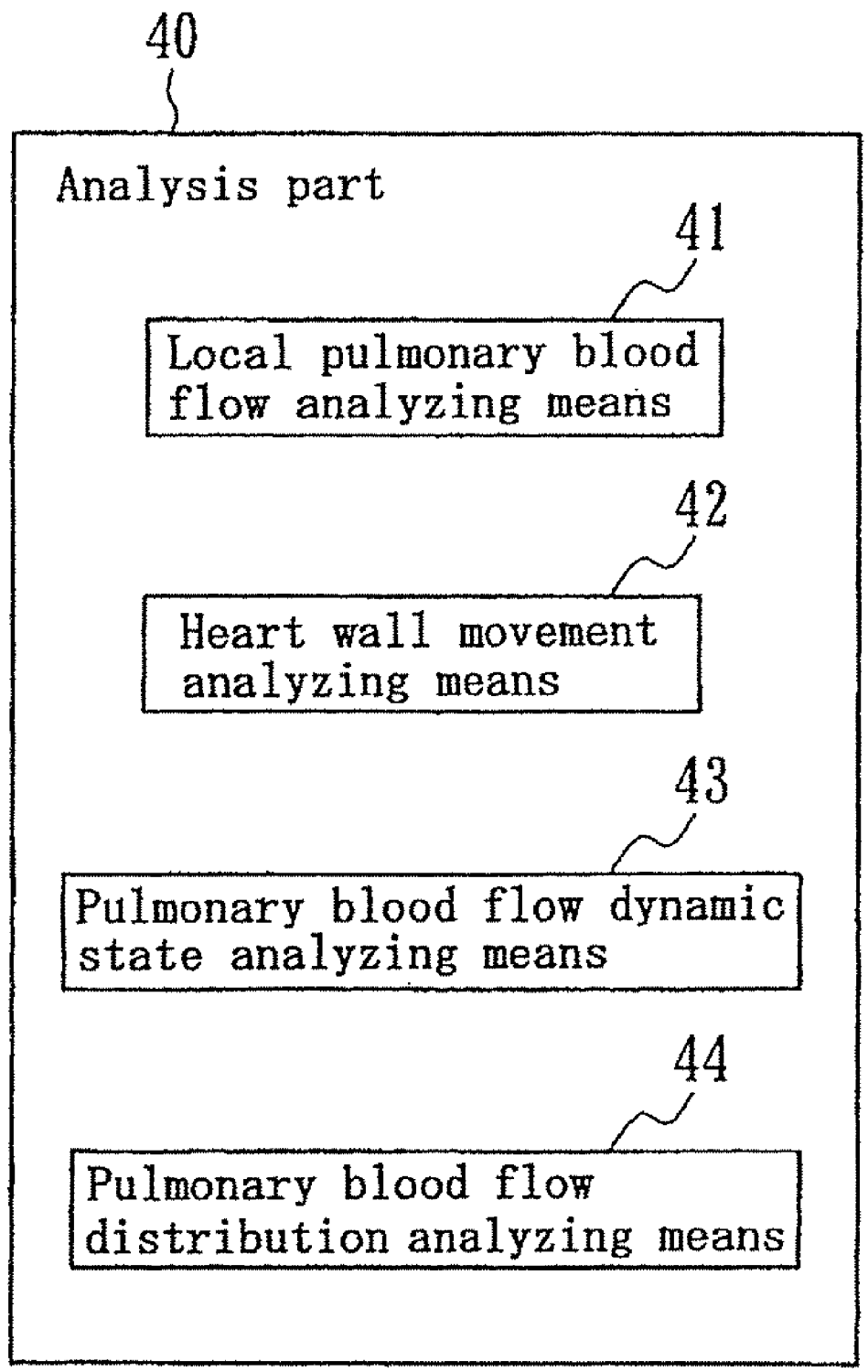
FIG. 3 is a block diagram illustrating a configuration of functions of an analysis part 40.
Figure 4:
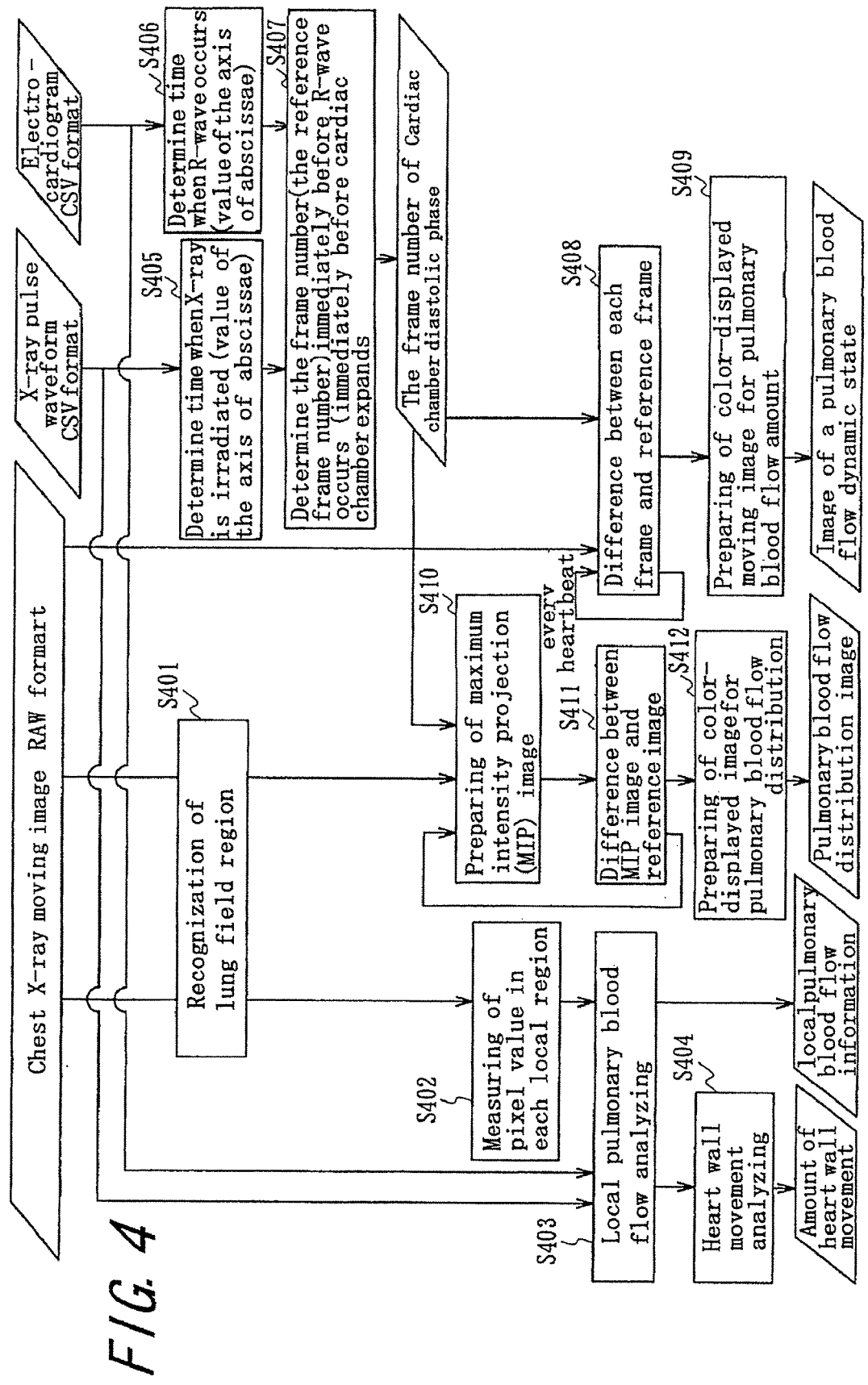
FIG. 4 is a flow chart illustrating processing of the analysis part 40.

FIG. 3 is a block diagram illustrating a configuration of functions of an analysis part 40 illustrated in FIG. 2. This analysis part 40 comprises local pulmonary blood flow analyzing means 41, heart wall movement analyzing means 42, pulmonary blood flow dynamic state analyzing means 43 and pulmonary blood flow distribution analyzing means 44. FIG. 4 is a flow chart illustrating processing of each means of the analysis part 40 illustrated in FIG. 3. Operations of such means will be described in detail below.

[Operation]

At first, an operation of the local pulmonary blood flow analyzing means 41 will be described. The local pulmonary blood flow analyzing means 41 recognizes the lung field region (step 401) to analyze pixel value variation (increase and decrease of the pulmonary blood flow) for a series of heart beats (steps 402 and 403), which will be described specifically below. A first average pixel value calculating technique according to the local pulmonary blood flow analyzing means 41 is processing of calculating an average pixel value for each lung in each frame of the chest X-ray moving image. By an operation of an operator, the local pulmonary blood flow analyzing means 41 reads a chest X-ray moving image from the chest X-ray moving image store 21, detects the boundary where the pixel value changes significantly on the read chest X-ray moving image to recognize the lung field region. For each lung (right lung and left lung), the average pixel values in those lung field region will be calculated. This operation is repeated for each frame to calculate the average pixel value for each lung.

A second average pixel value calculating technique according to the local pulmonary blood flow analyzing means 41 is processing of calculating an average pixel value for each lung in each region obtained by dividing the lung field region (divided region) for each frame. By an operation of an operator, the local pulmonary blood flow analyzing means 41 reads a chest X-ray moving image from the chest X-ray moving image store 21, detects the boundary where the pixel value changes significantly on the read chest X-ray moving image to recognize the lung field region. According to the operation of the operator, the above described recognized left and right lung field regions are divided into a plurality of regions. The average pixel value is calculated for each of the relevant divided regions. This operation is repeated for each frame to calculate the average pixel value for each of the divided regions.

A third average pixel value calculating technique according to the local pulmonary blood flow analyzing means 41 is processing of calculating an average pixel value for each of the arbitrarily designated measurement sites (region of interest (ROI)) for each frame. By an operation of an operator, the local pulmonary blood flow analyzing means 41 reads a chest X-ray moving image from the chest X-ray moving image store 21. And the average pixel value is calculated for each of the regions of interest designated by the operation of the operator such as mouse clicking. This operation is repeated for each frame to calculate the average pixel value for each of the regions of interest.

The local pulmonary blood flow analyzing means 41 calculates the average pixel value variation for one heart beat respectively for each lung field region (each lung) with the first average pixel calculating technique, for each of the divided regions with the second average pixel calculating technique and for each of the regions of interest with the third average pixel calculating technique and calculates the rate of change of pixel with the relevant variation and gradation. This pixel variation specifies a relative value of the pulmonary blood flow amount and the rate of change of pixel is calculated with the following equation (2).

$$A \text{ rate of change}(\%) = (\text{of average pixel value variation/gradation}) \times 100 \qquad (2)$$

Thereby, the pulmonary blood flow amount can be brought into comparison on each region. In this case, no pulmonary blood flow is present in the lung embolism site. Therefore, the variation and rate of change of average pixel value specifying the pulmonary blood flow amount is expected to drop. Therefore, information enabling effective use for a diagnosis of lung embolism can be obtained.

In addition, in the step 403, the local pulmonary blood flow analyzing means 41 reads X-ray pulse waveforms from the X-ray pulse waveform store 22 and an electrocardiogram from the electrocardiogram store 23 respectively with the operations of an operator. With the average pixel values, the X-ray pulse waveforms and the electrocardiogram respectively calculated with the techniques described above, the variation of average pixel value specifying pulmonary blood flow is analyzed and the temporal relation between the relevant average pixel value and electrocardiogram is analyzed.

Figure 5:
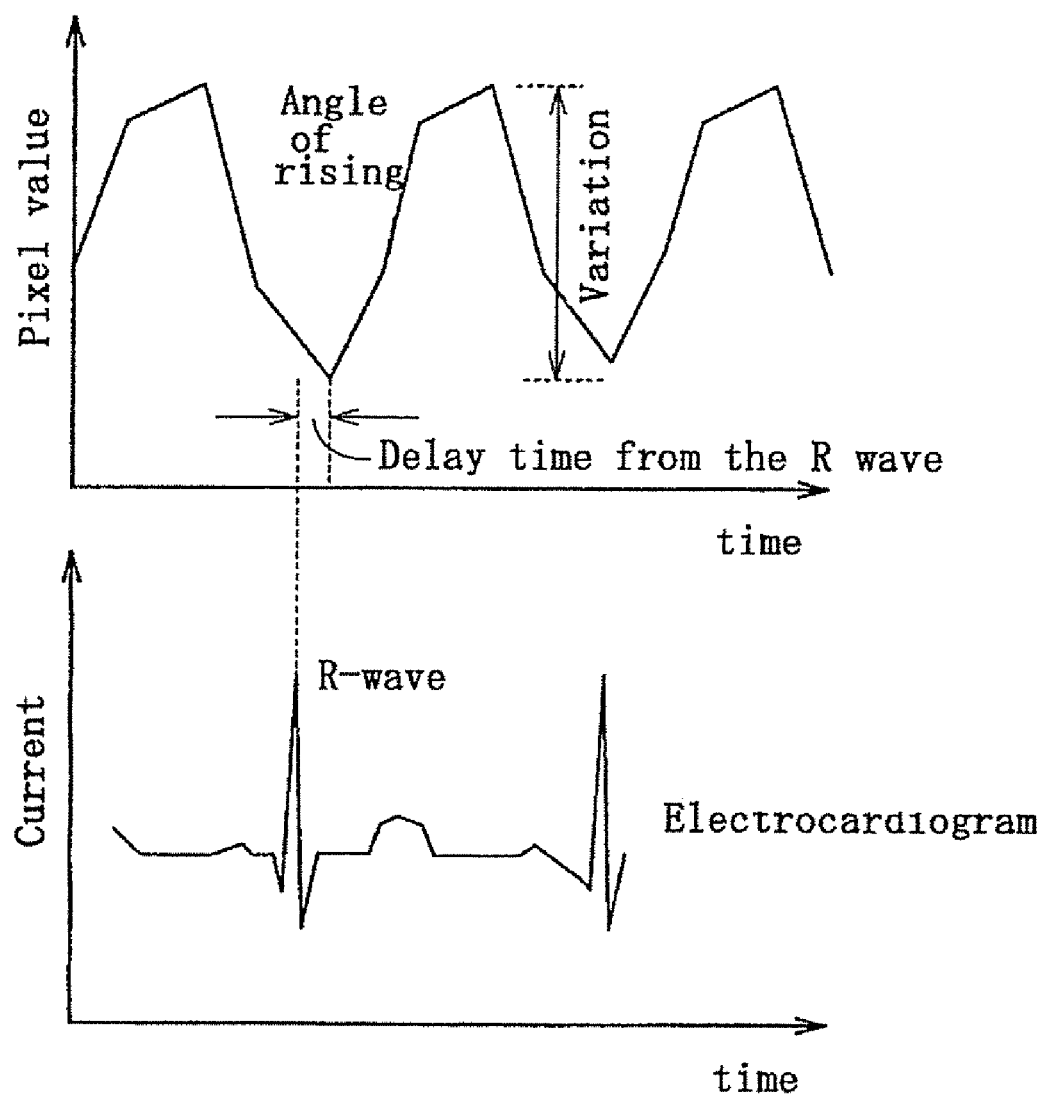
FIG. 5 includes diagrams illustrating an example of analysis result obtained by local pulmonary blood flow analyzing means 41.

FIG. 5 includes diagrams illustrating a result of analysis carried out by the local pulmonary blood flow analyzing means 41 on temporal relation between the average pixel value and electrocardiogram. The upper diagram illustrates a graph on the average pixel value and the bottom diagram illustrates an electrocardiogram. The local pulmonary blood flow analyzing means 41 calculates the temporal difference (delay time from the R wave) between the time point of the R wave in the electrocardiogram and the time point of the minimum value of the average pixel value. The delay time from the R wave, the circulation velocity of the pulmonary blood flow can be recognized. In addition, the rising angle from the time point of the minimum value of the average pixel value is calculated. This rising angle enables recognition of an increase of the velocity of the pulmonary blood flow. In addition, the difference (variation) between the minimum value and the maximum value of the average pixel values is calculated. Moreover, the local pulmonary blood flow analyzing means 41 calculates delay time from the R wave described above, the rising angle and the difference (variation) between the minimum value and the maximum value of the average pixel values for each lung, each of the divided regions and each of the regions of interest (not illustrated in the drawing). Thereby, the information hereof enables comparison among regions.

Figure 6:
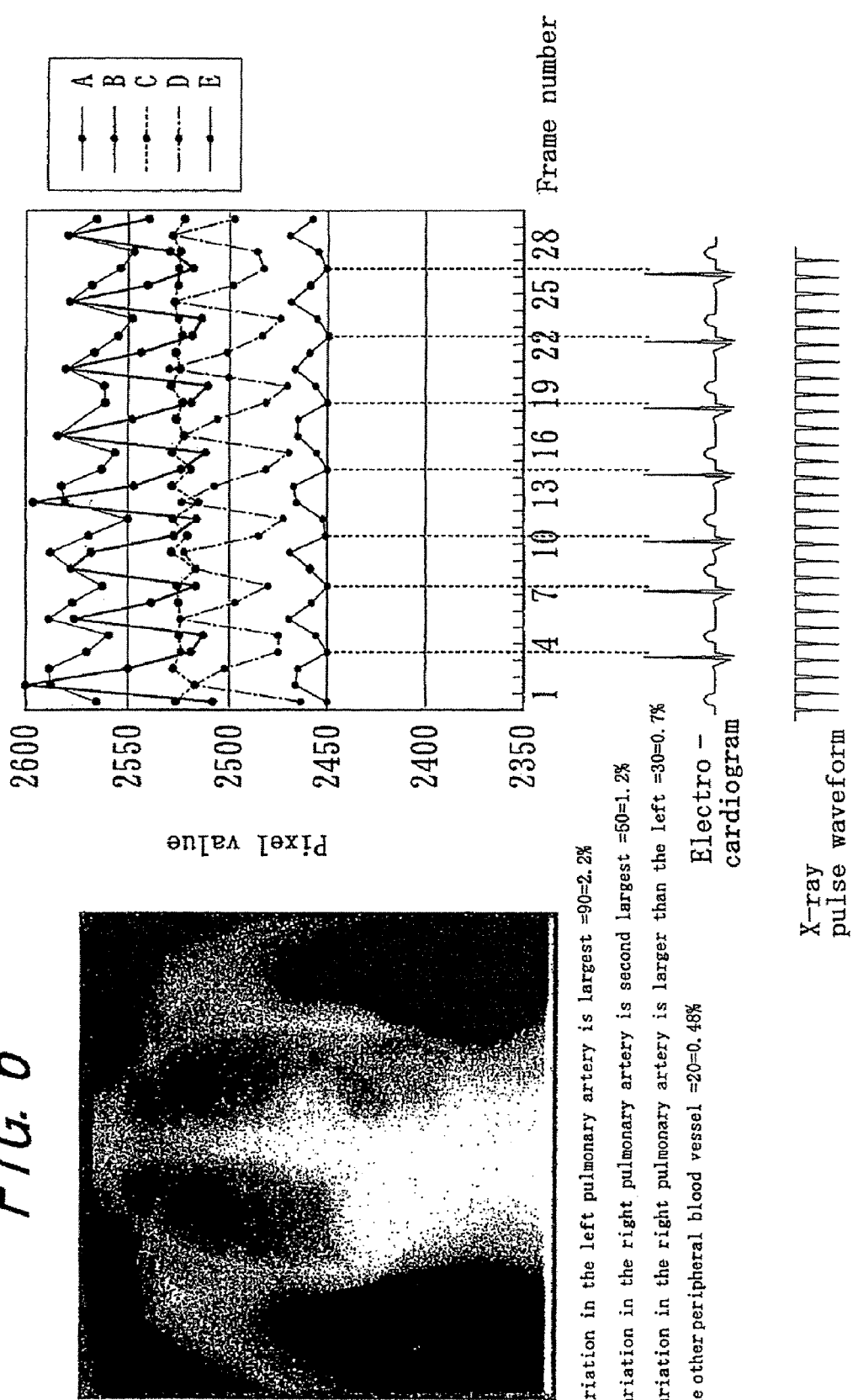
FIG. 6 includes diagrams illustrating local pulmonary blood flow information analyzed by the local pulmonary blood flow analyzing means 41.

The local pulmonary blood flow analyzing means 41 displays the local pulmonary blood flow the above described obtained by analysis on a screen. FIG. 6 is a screen image diagram specifying local pulmonary blood flow information analyzed by the local pulmonary blood flow analyzing means 41. In FIG. 6, the axis of abscissae of the graph specifies the axis of time. The axis of ordinates in the upper portion on the screen specifies the average pixel value. In the upper right portion on the screen, the average pixel value of the region of interest designated by an operation of an operator is displayed as a graph on each frame. The lower portion thereof displays an electrocardiogram and an X-ray pulse waveform which are associated with the axis of time. In addition, in the upper left on the screen, the region of interest in a chest X-ray moving image is displayed with black circle. In the lower portion thereof, a result of comparison on the average pixel values in the region of interest is displayed. For example, the quantity of variation of pixel of the region of interest with the largest variation in the left pulmonary artery is indicated to be 90 and the rate of change is indicated to be 2.2%. From FIG. 6, each of the average pixel values of the regions of interest corresponds to time when pulse of an X-pulse form occurs and apparently the average pixel value increases during the cardiac chamber systolic diastolic phase when the pulmonary blood flow flowing from the heart to the lung increases in the electrocardiogram illustrated in FIG. 15 and the average pixel value descends during the cardiac chamber diastolic phase when the pulmonary blood flow decreases. Likewise, the local pulmonary blood flow analyzing means 41 displays a graph on the average pixel value for each lung and a graph on the average pixel value for each of the divided regions. In addition, the local pulmonary blood flow analyzing means 41 displays the diagram illustrated in FIG. 5 on a screen as the local pulmonary blood flow information obtained by analysis.

Next, operations of the heart wall movement analyzing means 42 will be described. The heart wall movement analyzing means 42 determines the site of the heart wall to become the boundary of the lung field region based on the chest X-ray moving image to analyze the heart wall movement (step 404). Specifically, the heart wall movement analyzing means 42 automatically detects the site which is a boundary of the lung field region and where the pixel value is significantly changes in the site in the vicinity of the left cardiac chamber and right cardiac chamber designated by an operation of an operator to calculate the variation of that site as heart wall movement. Such calculation is carried out for each frame. The heart wall movement analyzing means 42 displays the heart wall movement for each of the designated regions and for each frame.

Figure 7:
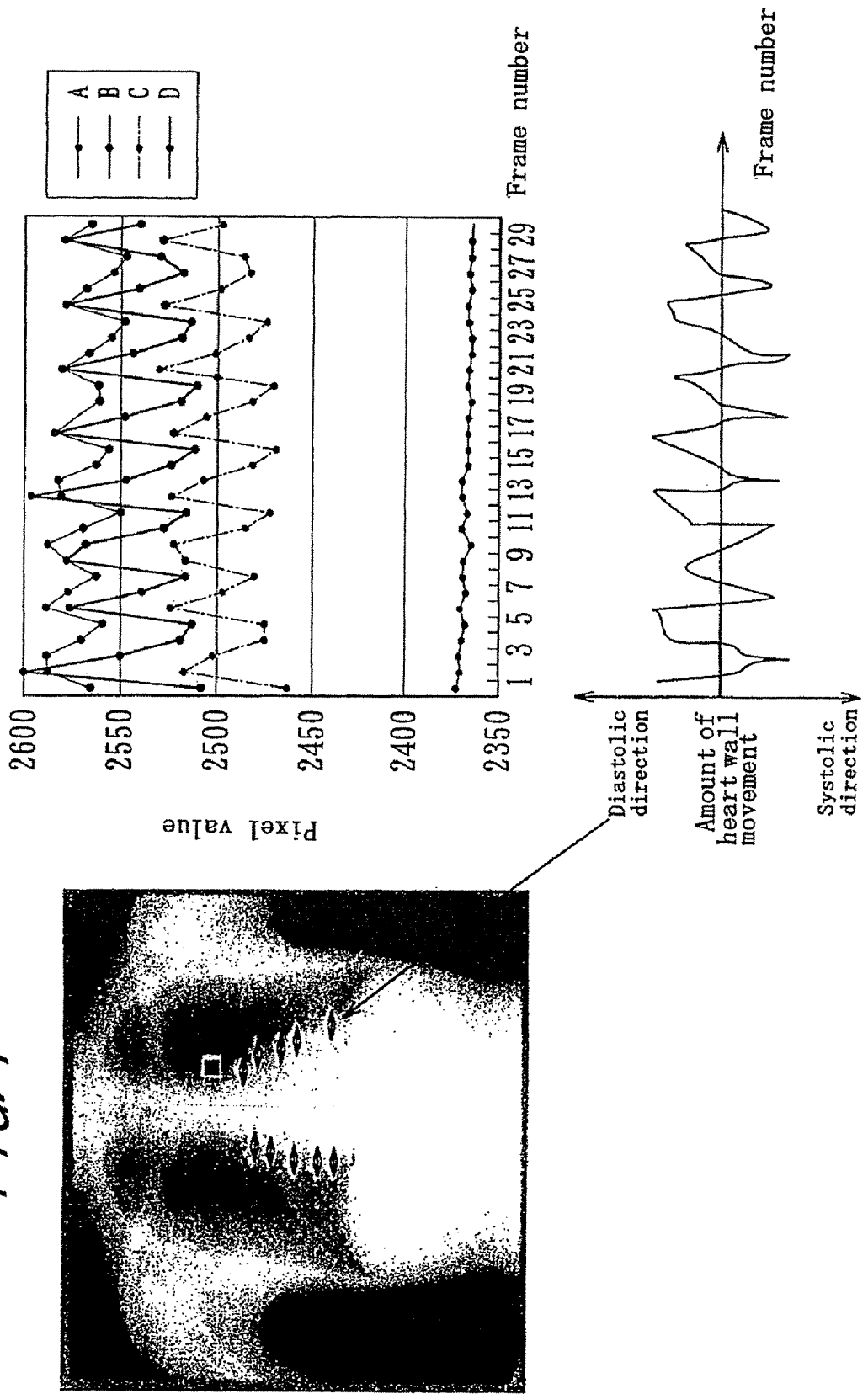
FIG. 7 includes diagrams illustrating heart wall movement analyzed by the heart wall movement analyzing means 42.

FIG. 7 is a screen image diagrams illustrating heart wall movement analyzed by the heart wall movement analyzing means 42. Here, as illustrated in FIG. 7, the heart wall movement can be displayed together with the average pixel value for each of the regions of interest. The display can be limited only to the heart wall movement. In FIG. 7, the axis of abscissae of the graph is the temporal axis and the axis of ordinates in the upper part of the screen specifies the average pixel value. In the lower right portion of the screen, heart wall movement of the site designated by an operation of an operator is displayed as a graph for each of the off frames. Apparently, the heart wall movement changes in the systolic direction during the cardiac chamber systolic phase and in the diastolic direction during the cardiac chamber diastolic phase respectively in the electrocardiogram shown in FIG. 15.

Figure 8:
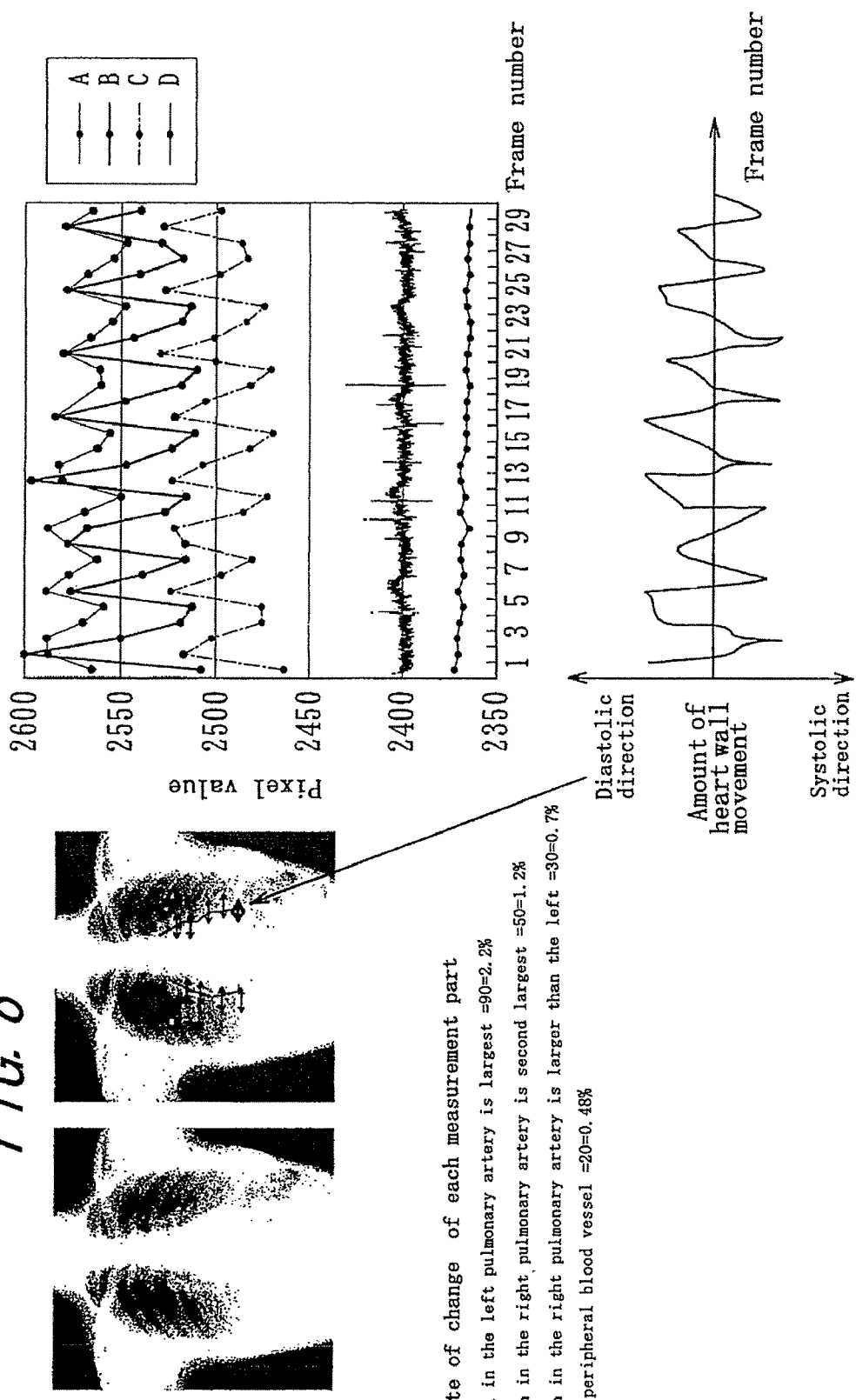
FIG. 8 includes diagrams illustrating local pulmonary blood flow information analyzed by the local pulmonary blood flow analyzing means 41 and heart wall movement analyzed by the heart wall movement analyzing means 42.

The analysis part 40 can display the local pulmonary blood flow information analyzed by the local pulmonary blood flow analyzing means 41 and the heart wall movement analyzed by the heart wall movement analyzing means 42 on the same screen. FIG. 8 is a screen image diagram illustrating local pulmonary blood information and heart wall movement. This diagram illustrates the case where FIG. 6 and FIG. 7 are displayed on the same screen and, therefore, detailed description will be omitted.

Next, operations of the pulmonary blood flow dynamic state analyzing means 43 will be described. The pulmonary blood flow dynamic state analyzing means 43 determines the frame immediately before an R wave occurs (immediately before the cardiac chamber expands) from the frame of one heart beat of a chest X-ray moving image to prepare an image of a pulmonary blood flow dynamic state based on the difference of pixel value between the relevant frame and another frame. Specifically, the pulmonary blood flow dynamic state analyzing means 43 reads, with operations of an operator, an X-ray pulse waveform from the X-ray pulse waveform store 22 and an electrocardiogram from an electrocardiogram store 23 respectively to determine time when X-ray is irradiated (value of the axis of abscissae) on the read X-ray pulse waveform (step 405). In addition, the time when the R-wave occurs (the value of the axis of abscissae) is determined for the read electrocardiogram (step 406). Consequently, the frame number immediately before the R-wave occurs is determined (step 407). Here, the frame immediately before the R-wave occurs is referred to as a reference frame. Here, in the following description, the frame immediately before the R-wave occurs is the reference frame and, nevertheless, does not necessarily have to be the immediately preceding frame but can be a frame at the timing of the R-wave in the electrocardiogram or a frame at the timing close thereto. That is, the frame (frame corresponding to the R wave) where the circumstance at the occurrence of an R wave in the electrocardiogram is reflected will be satisfactory.

Figure 9:
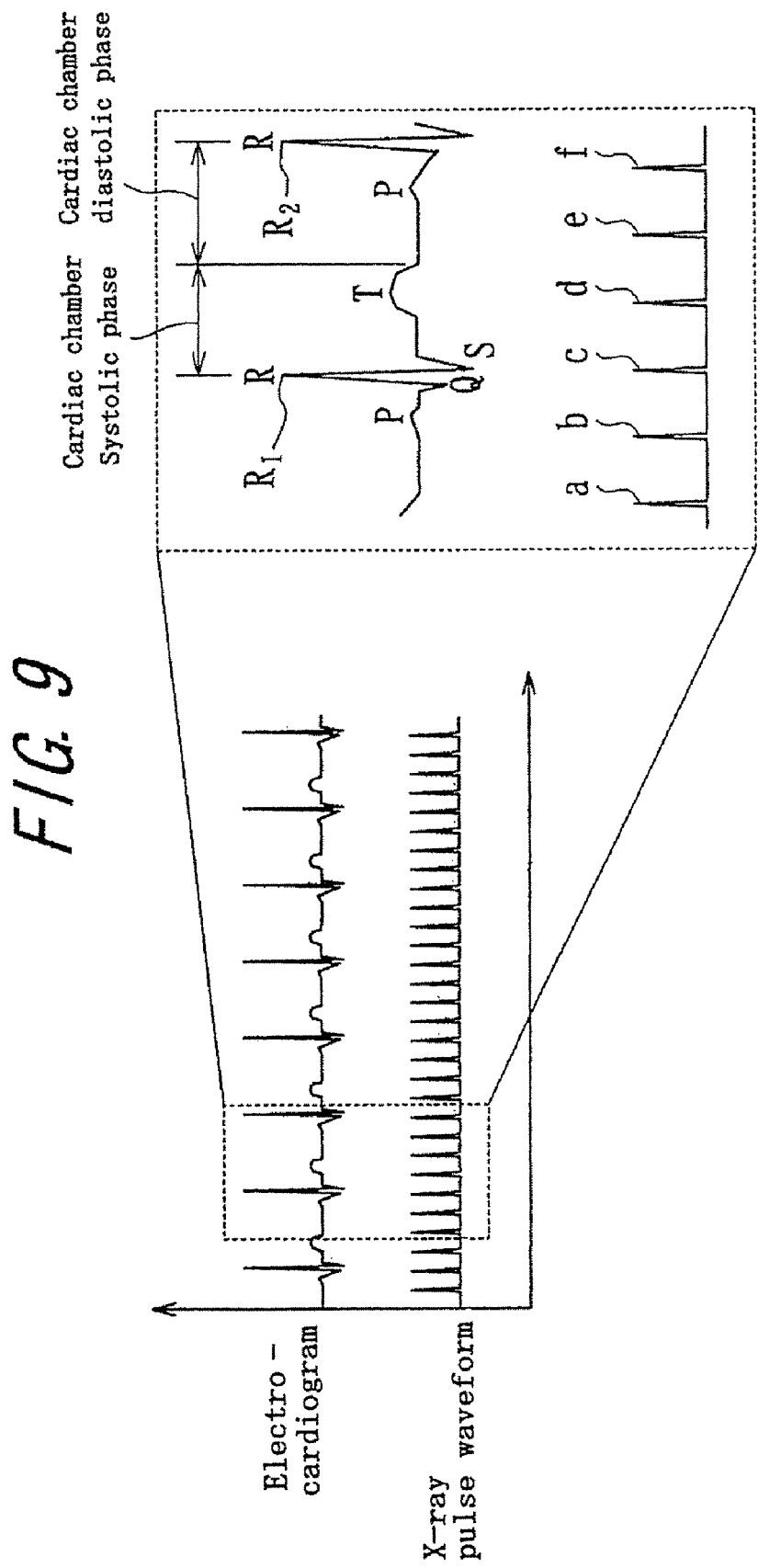
FIG. 9 includes diagrams illustrating a process of a step 407 in the flow chart illustrated in FIG. 4.

FIG. 9 includes diagrams illustrating a step 407 in the flow chart illustrated in FIG. 4. The right hand diagrams in FIG. 9 illustrate enlarged portions of the electrocardiogram and the X-ray pulse waveform illustrated in the left hand diagram. The upper portion thereof illustrates the electrocardiogram and the lower portion illustrates the X-ray pulse waveform. In that electrocardiogram, the site where the waveform protrudes upward is the R wave. In the X-ray pulse waveform, the site where the waveform protrudes upward is the timing when X-ray is irradiated. Here, the R wave consists of the pulse R1 and the pulse R2. The X-ray pulse waveform consists of the pulse a, the pulse b, the pulse c, the pulse d, the pulse e and the pulse f. In addition, the frame numbers Fa, Fb, Fc, Fd, Fe, Ff of the chest X-ray moving image picked up at the timings of the pulses a to f of the X-ray pulse waveform are not illustrated in the drawing. According to FIG. 9, the pulse b occurs immediately before the R1 wave. Since the pulse f occurs immediately before the R2 wave, the pulmonary blood flow dynamic state analyzing means 43 determines the frame numbers Fb and Ff as the frame numbers during the cardiac chamber diastolic phase. Here, in the step 405, the pulmonary blood flow dynamic state analyzing means 43 determines the time of the irradiation timing (timing time such as of pulses a to f) when the X-ray pulse waveform protrudes downwards and in the step 406, determines the time of the R waves (R1, R2 and the like) when the waveform in the electrocardiogram protrudes upward.

Back to FIG. 4, the pulmonary blood flow dynamic state analyzing means 43 calculates the difference of the pixel values between an image of a reference frame among the read chest X-ray moving images and an image of another frame for one heart beat on the basis of pixel unit with the following equation (3) to prepare an image of the pulmonary blood flow dynamic state (steps 408 and 409).

$$PVflow(n) = f(n) - f(n') \quad (3)$$

where PVflow is a function for preparing the image of the chest blood flow dynamic state; n is a frame number (0<n<30); f(n) is a chest X-ray moving image of the frame number n; n' is a reference frame number of the heat beat thereof; and f(n') is a chest X-ray moving image for the frame number n'. In FIG. 9, the image of the pulmonary blood flow dynamic state is prepared based on the difference of the pixel values between the image of the frame number Fb being a reference frame and images of the frame numbers Fc, Fd, Fe and Ff. The case where the difference of the pixel value is positive (the average pixel value increases=X-ray permeability decreases=the pulmonary blood flow increases) is indicated by a warm color. The case where the difference of the pixel value is negative (the average pixel value decreases=X-ray permeability increases=the pulmonary blood flow decreases) is indicated by a cold color. The image of the pulmonary blood flow dynamic state is illustrated by contrasting density matched with the amount of the difference and the electrocardiogram and the X-ray pulse waveform is displayed on the screen together with the relevant image of the pulmonary blood flow dynamic state (step 409).

Figure 10:
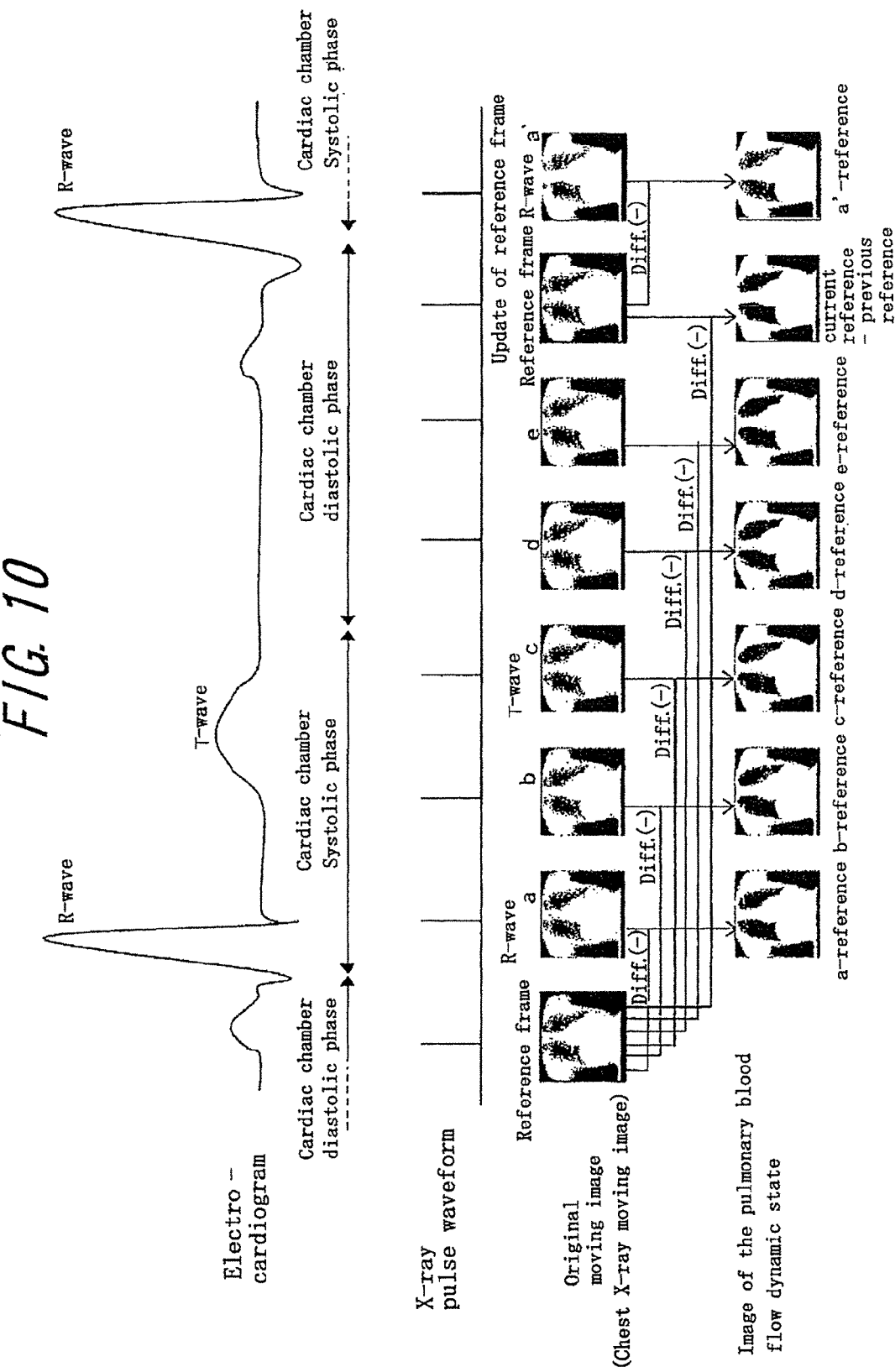
FIG. 10 illustrates a computer algorithm for producing images of a pulmonary blood flow dynamic state with pulmonary blood flow dynamic state analyzing means 43.

FIG. 10 illustrates a computer algorithm for producing images of a pulmonary blood flow dynamic state with pulmonary blood flow dynamic state analyzing means 43. In FIG. 10, the axes of abscissae in the graphs represent temporal axes. In a descending order from the top, the electrocardiogram, the X-ray pulse waveform, the chest X-ray moving images, the images of the pulmonary blood flow dynamic state in which the difference of the pixel values is indicated in color with contrasting density are displayed. The images of the pulmonary blood flow dynamic states are prepared respectively based on the differences of the pixel values between the reference frame, the frames a, b, c, d, e and the reference frame of the next heart beat and are prepared respectively based on the differences of the pixel values between the reference frame after updating and the frames a', b' and the like when the reference frame is updated. Since the periods during the cardiac chamber systolic and diastolic phases can be grasped by the electrocardiogram as illustrated in FIG. 15, the pixel variation, that is, the level of increase and decrease of the pulmonary blood flow, of the image of the pulmonary blood flow dynamic state for each time can be recognized on the basis of pixel unit.

Figure 11:
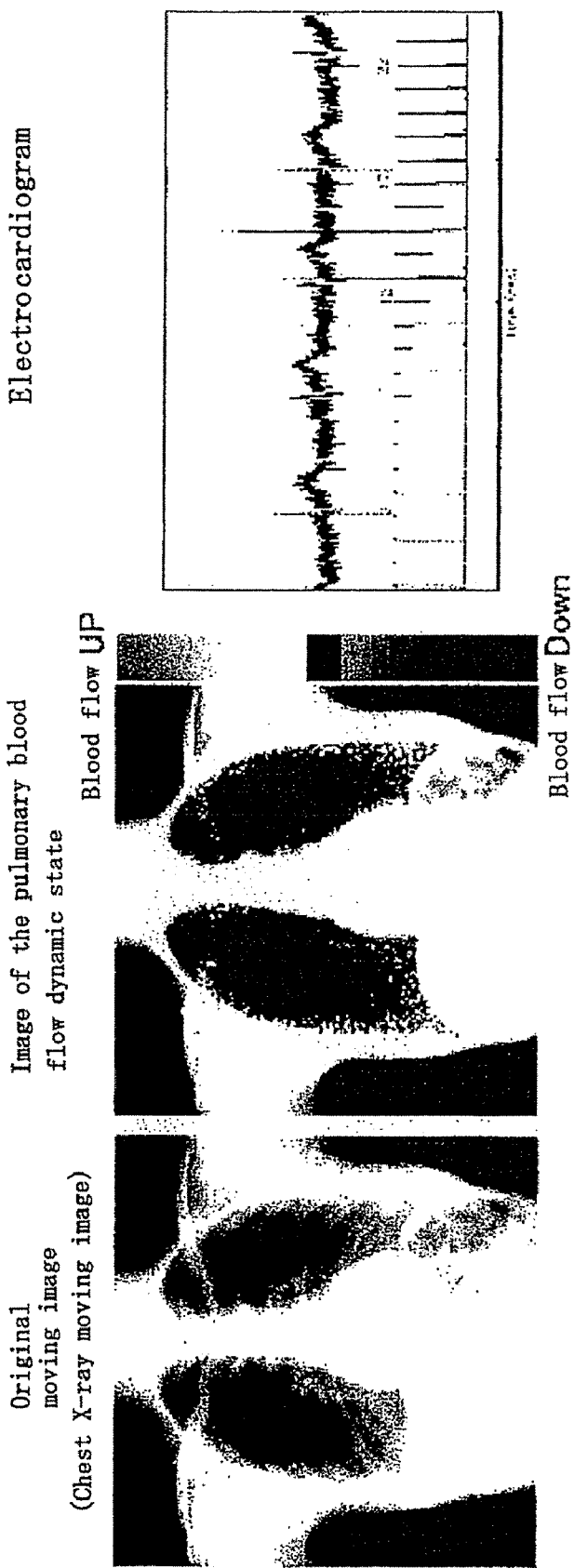
FIG. 11 includes diagrams illustrating images of a pulmonary blood flow dynamic state analyzed by the pulmonary blood flow dynamic state analyzing means 43.

In addition, FIG. 11 is a screen image diagrams illustrating images of a pulmonary blood flow dynamic states analyzed by the pulmonary blood flow dynamic state analyzing means 43. In FIG. 11, an electrocardiogram is displayed on the right side. A chest X-ray moving image and an image of the pulmonary blood flow dynamic state are displayed on the left side. By moving the vertical scroll bar (not illustrated in the drawing) on the electrocardiogram along the temporal axis, the pulmonary blood flow dynamic state image display part displays an image of pulmonary blood flow dynamic state prepared from the difference in the pixel values between a reference frame and a frame at the site where the scroll bar crosses the temporal axis.

Next, operations of the pulmonary blood flow distribution analyzing means 44 will be described. The pulmonary blood flow distribution analyzing means 44 prepares maximum intensity projection (MIP) image from each frame of a chest X-ray moving image of one heart beat and prepares a pulmonary blood flow distribution image based on the difference of pixel value between the MIP image and an image of a reference frame. Specifically, at first, the pulmonary blood flow distribution analyzing means 44 executes likewise processing of the steps 405, 406 and 407 in the pulmonary blood flow dynamic state analyzing means 43. That is, the pulmonary blood flow distribution analyzing means 44 reads, with operations of an operator, an X-ray pulse waveform from the X-ray pulse waveform store 22 and an electrocardiogram from an electrocardiogram store 23 respectively to determine time when X-ray is irradiated on the X-ray pulse waveform (step 405); determines the time when the R-wave occurs for the electrocardiogram (step 406); and determines the number of the reference frame is (step 407).

The pulmonary blood flow distribution analyzing means 44 prepares an MIP image every heart beat based on the each frame of the chest X-ray moving image read from the chest X-ray moving image store 21 and the reference frames determined in the steps 405 to 407 (step 410). Specifically, each frame for every one beat, the maximum value is projected in the direction of temporal axis for every pixel to prepare one piece of MIP image. In FIG. 9, since the reference frame numbers are Fb and Ff, the MIP image in the heart beat including the reference frame of Fb is prepared based on the image of frames from the reference frame number Fb to the frame number Fe being the first preceding frame number Fe of the next reference frame number Ff.

Next, the pulmonary blood flow distribution analyzing means 44 calculates difference of the pixel value between the MIP image prepared in the step 410 and the image of the reference frame for every heart beat with the following equation (4) to calculate for every pixel (step 411). Here, one heart beat refers to the duration from a reference frame to the next reference frame.

$$PV\text{dis}(n')=\text{MIP}(n')-f(n'') \tag{4}$$

where PVdis is a function for preparing the chest blood flow distribution image; n' is a serial number during the cardiac chamber diastolic phase (0<n'<number of times during the cardiac chamber diastolic phase); MIP is a function for preparing an MIP image; n" is a reference frame for that heart beat; f(n") is the n"-th chest X-ray moving image. In FIG. 9, the pulmonary blood flow distribution image for the frames Fb, Fc, Fd and Fe is prepared based on the difference of the pixel values between MIP image for that heart beat and the reference frame for that heart beat (chest X-ray moving image with the frame number Fb).

The pulmonary blood flow distribution analyzing means 44 prepares a static image obtained by colored display for the pulmonary blood flow for the pulmonary blood flow distribution image prepared in step 411 (step 412). In that case, contrasting density in color is provided corresponding to the calculated difference so that the case with the large difference is displayed to be thick and the case with small difference is displayed to be thin.

Figure 12:
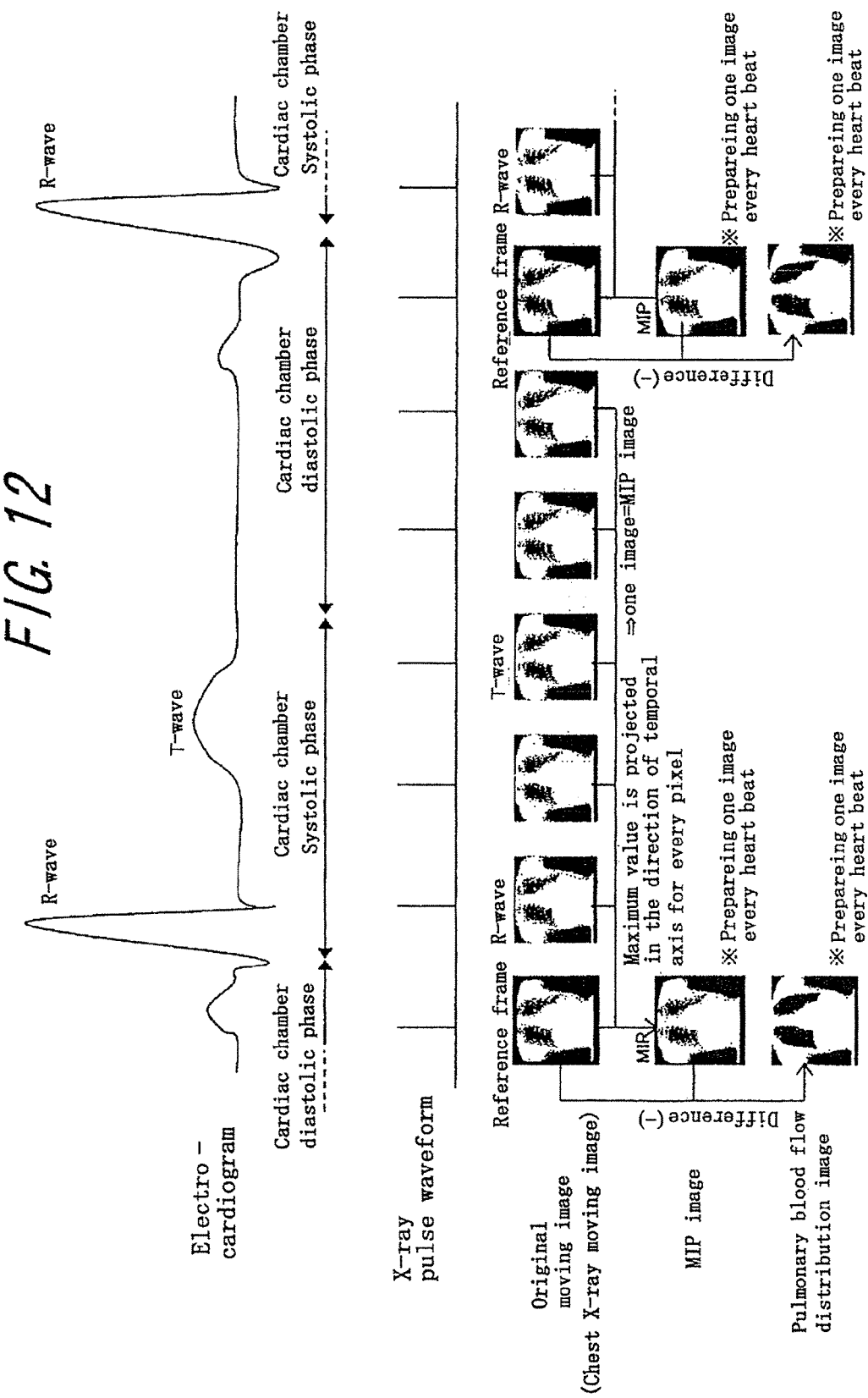
FIG. 12 illustrates a computer algorithm for producing pulmonary blood flow distribution images with pulmonary blood flow distribution analyzing means 44.

FIG. 12 illustrates a computer algorithm for producing pulmonary blood flow distribution images with pulmonary blood flow distribution analyzing means 44. In FIG. 12, the axes of abscissae of the graph specify the temporal axes. In a descending order from the top, the electrocardiogram, the X-ray pulse waveform, the chest X-ray moving images, the MIP images, the pulmonary blood flow distribution images in which the difference of the pixel values is indicated in color in contrasting density are displayed. The MIP image is prepared from a reference frame and frames a to e. The pulmonary blood flow distribution images are prepared respectively based on the differences of the pixel values between the MIP images and the image of the reference frame. When the reference frame is updated, the MIP images are prepared from the reference frame after updating and the frames a' to e'. The pulmonary blood flow distribution images are prepared from those MIP images and the reference frames.

Figure 13:
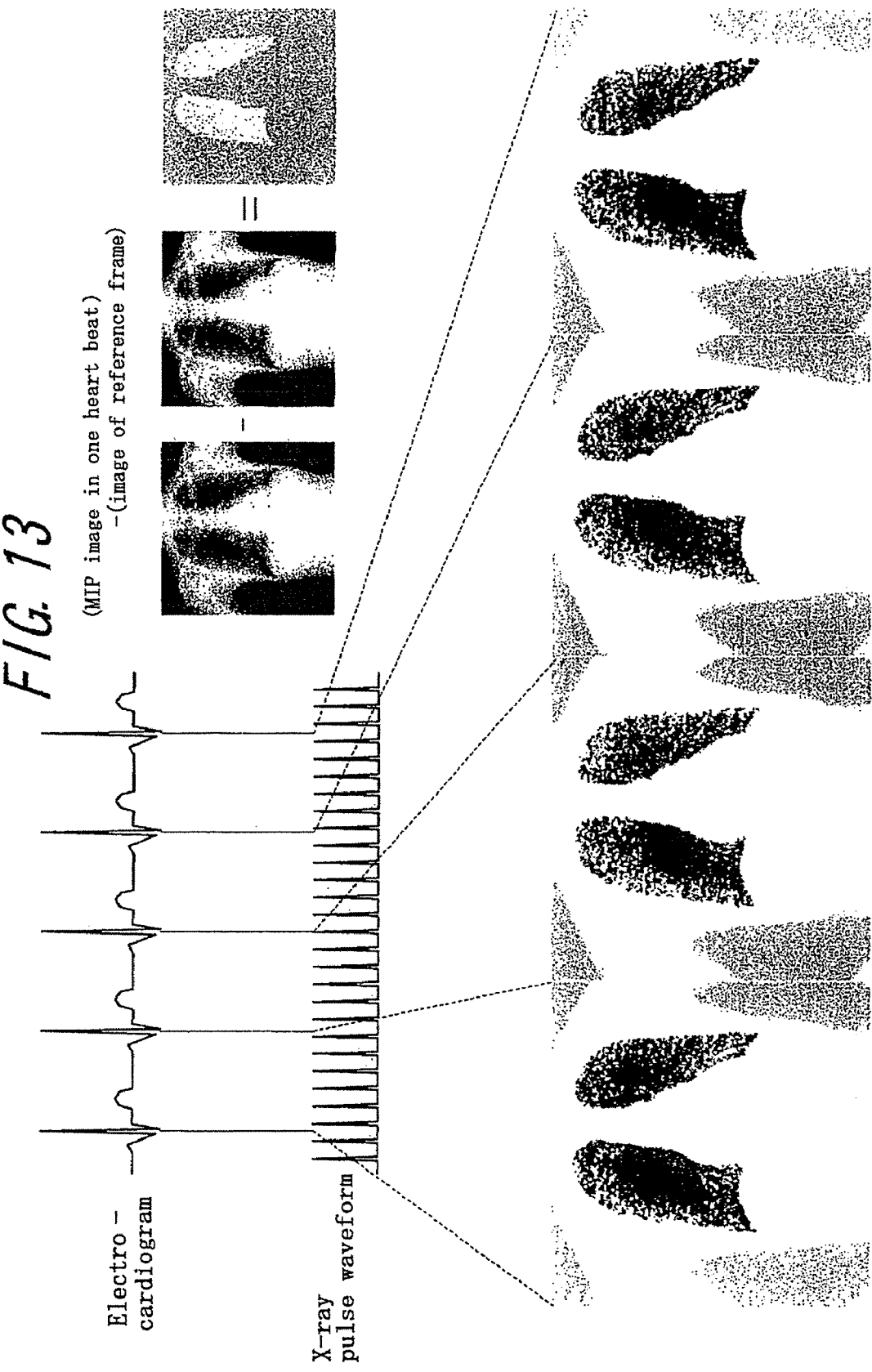
FIG. 13 illustrates first diagrams illustrating pulmonary blood flow distribution images analyzed by the pulmonary blood flow distribution analyzing means 44.
Figure 14:
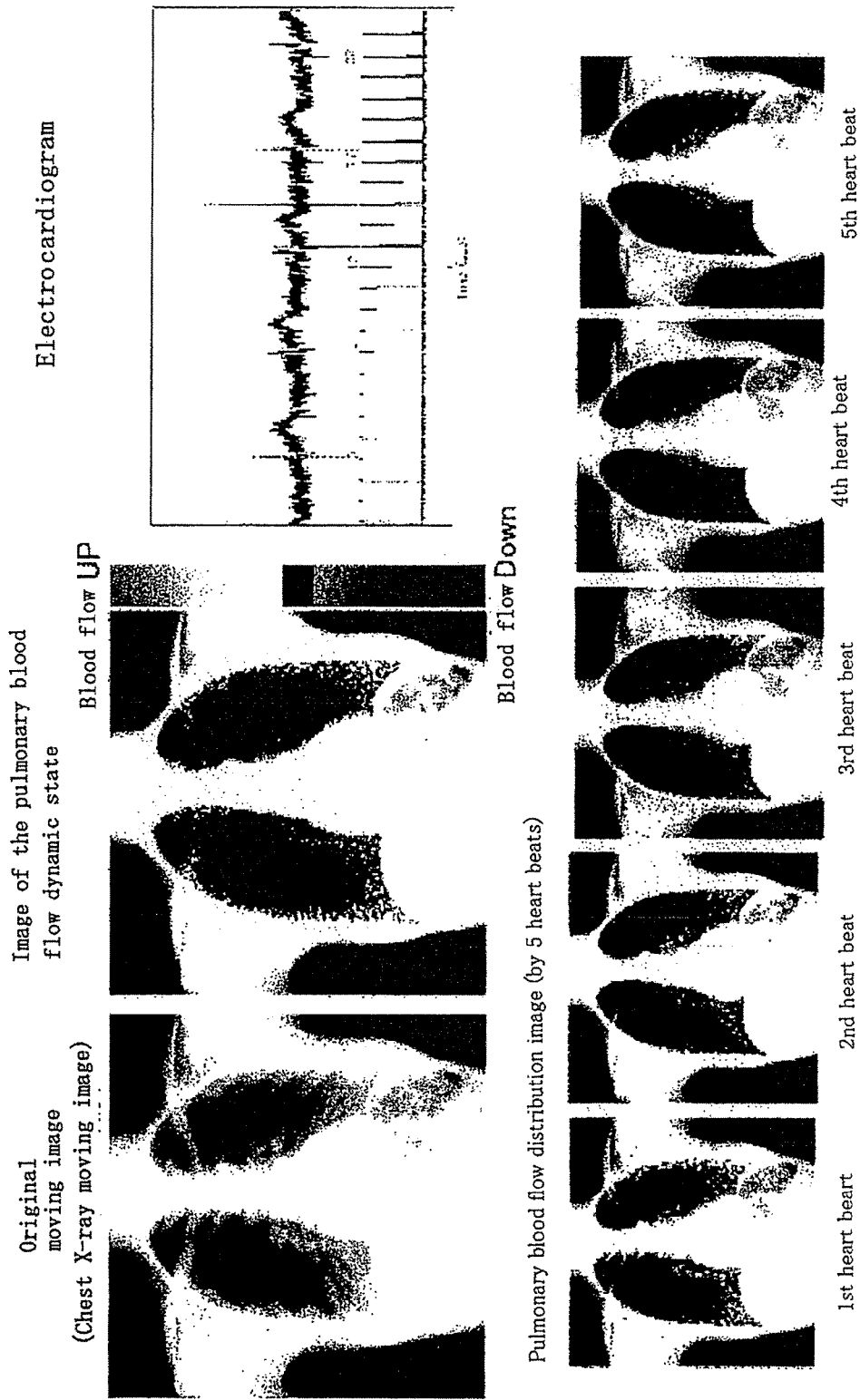
FIG. 14 illustrates second diagrams illustrating pulmonary blood flow distribution images analyzed by the pulmonary blood flow distribution analyzing means 44.

FIG. 13 is a screen image diagram illustrating diagrams illustrating first pulmonary blood flow distribution images analyzed by the pulmonary blood flow distribution analyzing means 44. Those diagrams are obtained by extending the temporal axis of the graph illustrated in FIG. 12 to chronologically display the pulmonary blood flow distribution images for each heart beat. FIG. 14 is a screen image diagram illustrating diagrams illustrating second pulmonary blood flow distribution images analyzed by the pulmonary blood flow distribution analyzing means 44. Those diagrams are obtained by displaying the pulmonary blood flow distribution images for the first heart beat to the fifth heart beat in addition to the screen image diagrams illustrated in FIG. 11. According to FIGS. 12 to 14, the total blood flow can be grasped from the pulmonary blood flow distribution images, which corresponds to the pulmonary blood flow scintigraphy. Thereby, the total blood flow for every heart beat can be assessed. For example, it is expected that the site where little pulmonary blood flow is present is displayed to be faint since the value for the difference between the pixel values is small and the site where little pulmonary blood flow is present lacks in colored display. Accordingly, information effectively utilizable for a diagnosis on a lung embolism can be obtained by the pulmonary blood flow distribution analyzing means 44.

So far, the present invention has been described with an embodiment. However, the present invention will not be limited to the above described embodiment but various variations can be made therein without departing the spirit and intention thereof. For example, the continuous X-ray image screening examination device 1 illustrated in FIG. 1 and FIG. 2 is configured by one computer but can be configured by a plurality of computers. For example, the continuous X-ray image screening examination device 1 can be configured by a chest X-ray moving image store 21, an X-ray pulse waveform store 22, an information storing appliance comprising various types of information of the electrocardiogram store 23, a controlling appliance comprising the control part 30 and an analyzing appliance comprising the analysis part 40 and be respectively brought into connection by a network.

In addition, in the continuous X-ray image screening examination device 1 illustrated in FIG. 1 and FIG. 2, the control part 30 inputs an electrocardiogram from the electrocardiogram recording apparatus 5 to store in the electrocardiogram store 23; the analysis part 40 reads an electrocardiogram from the electrocardiogram store 23 to determine the time when the R wave occurs to determine a reference frame. In this case, the continuous X-ray image screening examination device 1 does not have to use an electrocardiogram in order to determine a reference frame. Specifically, the continuous X-ray image screening examination device 1 can determine the time when the R wave occurs based on the average pixel value of a lung to determine the reference frame and can determine the time when the R wave occurs based on heart wall movement to determine the reference frame.

Figure 16:
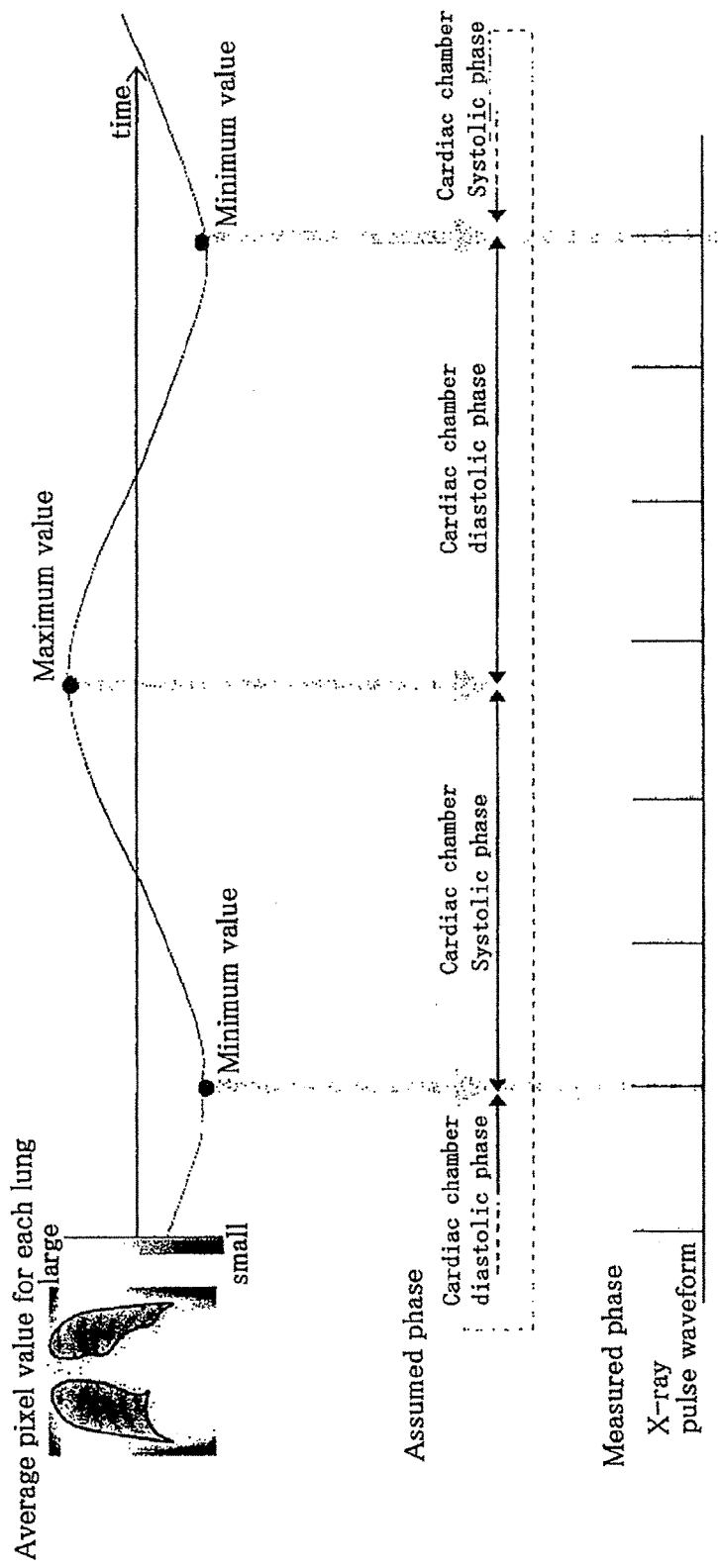
FIG. 16 includes diagrams illustrating a technique of determining a reference frame based on the average pixel value of a lung.

FIG. 16 includes diagrams illustrating a technique of determining a reference frame based on the average pixel value of a lung. There is high relativity between the pulmonary pixel value and the heart beat phase. By using this nature, the heart beat phase can be assumed and the time when an R wave occurs can be determined. As illustrated in FIG. 16, the period when the pulmonary average pixel value varies from the minimum value to the maximum value corresponds to the cardiac chamber systolic phase. The period of variation from the maximum value to the minimum value corresponds to the cardiac chamber diastolic phase. Accordingly, since the time when the pulmonary average pixel value will reach the minimum value is time when the R wave occurs, the continuous X-ray image screening examination device 1 can determine the frame immediately before the time when the average pixel value reaches the minimum value as the reference frame.

Figure 17:
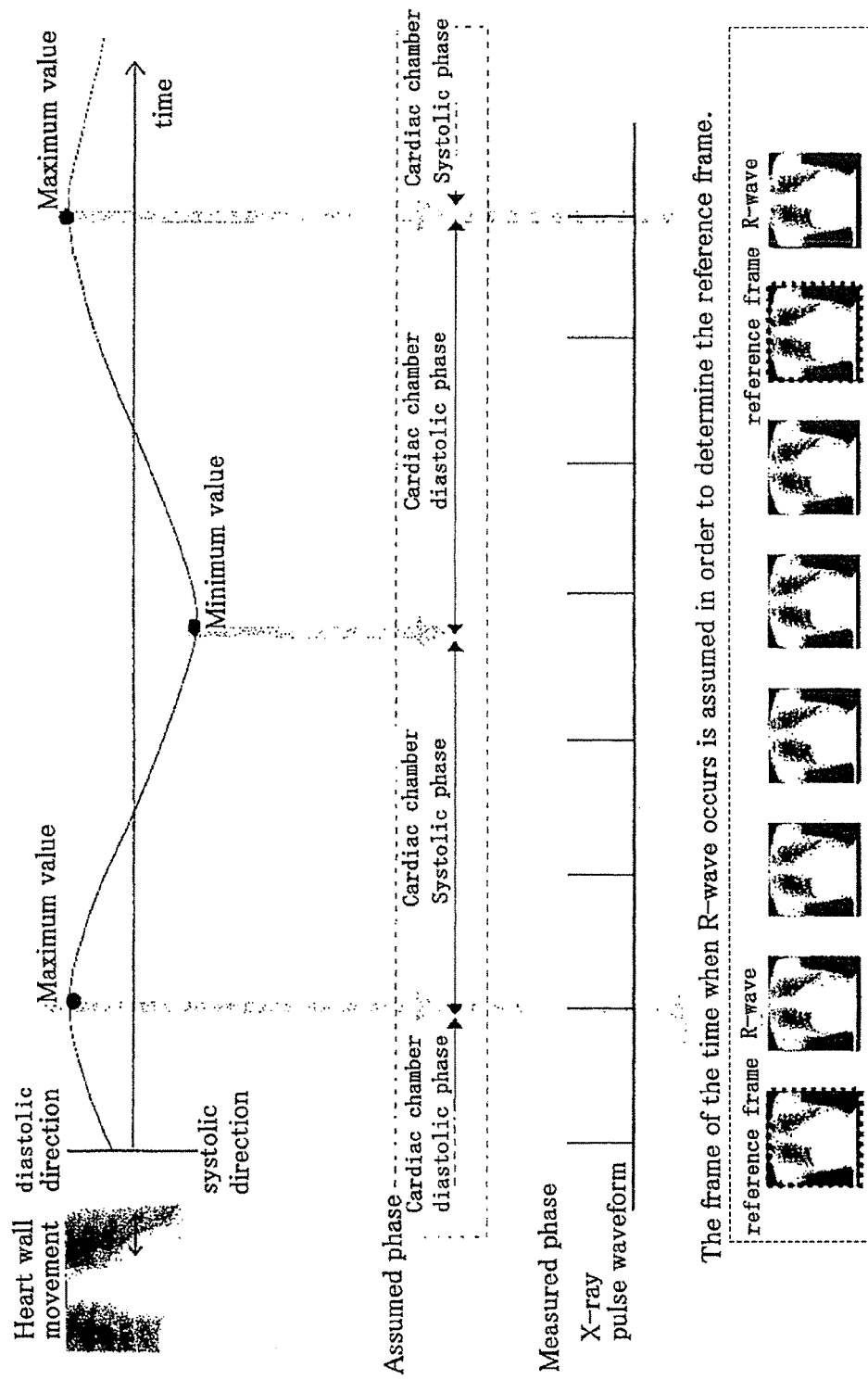
FIG. 17 includes diagrams illustrating a technique for determining a reference frame based on heart wall movement.

FIG. 17 includes diagrams illustrating a technique for determining a reference frame based on heart wall movement. The heart beat phase is assumed form the heart wall movement and, thereby, the time when the R wave occurs can be determined. As illustrated in FIG. 17, with the direction of expansion of a heart being + and the direction of contraction thereof being − in the heart wall movement, the period when the heart wall movement varies from the maximum value to the minimum value corresponds to the cardiac chamber systolic phase. The period of variation from the minimum value to the maximum value corresponds to the cardiac chamber diastolic phase. Accordingly, since the time when the heart wall movement reaches the maximum value is the time when the R wave occurs, the continuous X-ray image screening examination device 1 can determine the frame immediately before the time when the heart wall movement reaches the maximum value as the reference frame.

In addition, in the continuous X-ray image screening examination device 1 illustrated in FIG. 1 and FIG. 2, the local pulmonary blood flow analyzing part 41 of the analysis part 40, the pulmonary blood flow dynamic state analyzing part 43 and the pulmonary blood flow distribution analyzing part 44 carries out analysis and processing with pulmonary blood flow as an object. However, the analysis can be carried out with cardiac blood flow as an object. Here, the local pulmonary blood flow analyzing part 41, the pulmonary blood flow dynamic state analyzing part 43 and the pulmonary blood flow distribution analyzing part 44 will respectively become a local cardiac blood flow analyzing means, a cardiac blood flow dynamic state analyzing part and a cardiac blood flow distribution analyzing part.

In that case, the local cardiac blood flow analyzing means analyzes variation of the pixel value in the mediastinal part. Here, the mediastinal part refers to a portion which is located in the middle of the left and right lungs and is surrounded by costa, chest and the like likewise a lung. Specifically, the mediastinal part refers to cardiac chambers, cardiac atriums, cardiac muscles and heart walls configuring a heart, a large vessel system such as superior vena cava, inferior vena cava and the aorta brought into connection and, moreover, lymph nodes and the like.

FIGS. 18(1) and 18(2) are diagrams illustrating a mediastinal part analyzed by local cardiac blood flow analyzing means. FIG. 18(1) is a diagram illustrating a configuration of a heart. FIG. 18(2) is a diagram illustrating positions of respective parts in one frame of a chest X-ray moving image. Accompanied by expansion and constriction of the cardiac chamber, the atrioventricular valves, the aorta valve and the pulmonary aorta valve open and close. By variation of left ventricular pressure, left atrial pressure, right ventricular pressure and right atrial pressure, blood flow dynamic state information of a heart such as an cardiac output can be obtained as described below.

Figure 19:
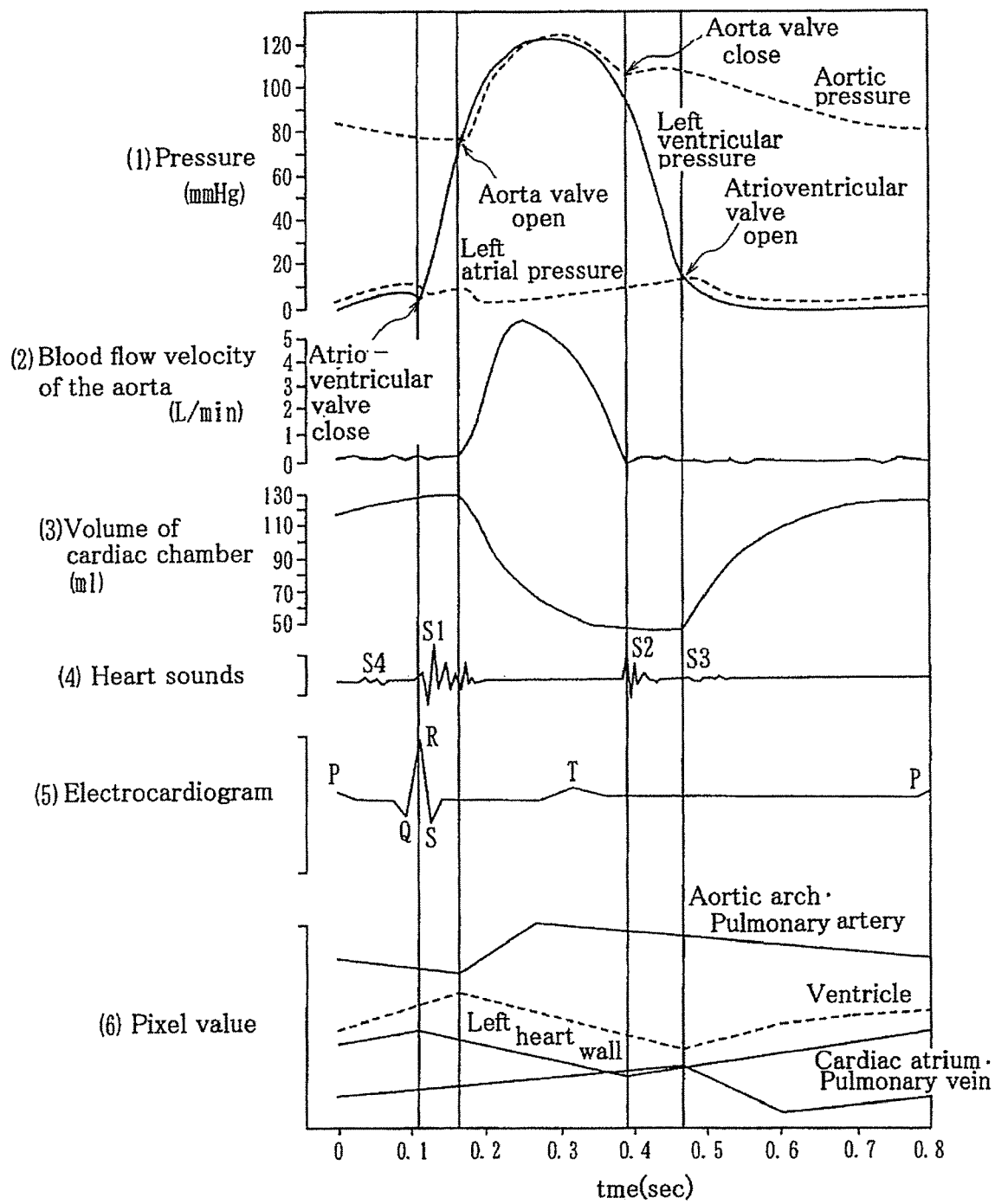
FIG. 19 is a diagram illustrating blood flow dynamic state information of a mediastinal part analyzed by the local cardiac blood flow distribution analyzing means.

FIG. 19 is a diagram illustrating blood flow dynamic state information of a mediastinal part analyzed by the local cardiac blood flow distribution analyzing means. In FIG. 19, respectively FIG. 19(1) illustrates pressure in each of the aorta, the left cardiac chamber, the left cardiac atrium; FIG. 19(2) illustrates blood flow velocity of the aorta; FIG. 19(3) illustrates volume of left cardiac chamber; FIG. 19(4) illustrates heart sounds; FIG. 19(5) illustrates electrocardiograms; FIG. 19(6) illustrates average pixel values at respective site in a heart. The axis of abscissae represents time. An average pixel value calculation technique with the local pulmonary blood flow analyzing means 41 in each place in a heart is processing to calculate an average pixel value for each of the measurement site (region of interest (ROI)) such as the aortic arc, the pulmonary aorta and the left cardiac chamber designated by an operation of an operator in each frame of a chest X-ray moving image. Specifically, the local pulmonary blood flow analyzing means 41 reads a chest X-ray moving image from the chest X-ray moving image store 21 by an operation of an operator. And in the first frame, the average pixel value is calculated for each of the regions of interest such as the aortic arc designated by the operation of the operator such as mouse clicking. For the second frame and thereafter, the average pixel value is calculated for the same region of interest as for the first frame and the graph on the pixel value illustrated in FIG. 19(6) is displayed on the screen.

Next, with reference to FIGS. 19(1) to 19(5), operations of one beat of a heart will be described. At first, an atrioventricular valve gets closed. Then, the heart sound (4) will form a waveform S1 so that the electrocardiogram (5) gives rise to an R wave. When the cardiac chamber systolic phase starts, the cardiac chamber starts contracting so as to drastically increase the pressure (1) in a left cardiac chamber so that an aorta valve will get open. During this period, the cardiac chamber volume (3) remains constant. When the aorta valve gets open, the cardiac chamber volume (3) gets smaller so that the aorta blood flow velocity (2) gets larger. Being accompanied thereby, the pixel value (6) of the aortic arc and pulmonary aorta increases so that the pixel value (6) of the cardiac chamber decreases. When the aorta blood flow velocity (2) starts decreasing, the left cardiac chamber pressure (1) also decreases so that the aorta valve will get closed. When the cardiac chamber diastolic phase starts, the cardiac chamber starts expanding so as to drastically decrease the pressure (1) in the left cardiac chamber so that heart sound (4) will form a waveform S2. During this period, the cardiac chamber volume (3) remains constant. And when an atrioventricular valve gets open, the cardiac chamber volume (3) increases drastically. Being accompanied thereby, the pixel value (6) of the cardiac chamber increases so that the pixel value (6) of a cardiac atrium and pulmonary vena cava decreases.

Thus, the pixel values in the respective sites in a heart illustrated in FIG. 19(6) will appear as a change in a reflection of operations of one heart beat of the heart in FIG. 19(1) to FIG. 19(5). There is strong relation between the change of those pixel values and the change of blood flow. For example, the portion where the variation of the pixel value illustrated in FIG. 19(6) decreases can be determined to be a portion where the blood flow decreases or no blood flow is present, which can be used as useful information for a diagnosis such as of a lung embolism or a heart disease. In addition, such information can be used as useful information for management during and after that operation.

In the continuous X-ray image screening examination device 1 illustrated in FIG. 1 and FIG. 2, with the frame immediately before occurrence of the R wave being a reference frame, the pulmonary blood flow dynamic state analyzing means 43 of the control part 30 prepares an image of the pulmonary blood flow dynamic state based on the difference of pixel values between the relevant reference frame and the other frames. However, the image of the pulmonary blood flow dynamic state can be prepared based on the difference of pixel values between mutually adjacent frames. Likewise, the cardiac blood flow dynamic state analyzing means can prepare an image of the cardiac blood flow dynamic state based on the difference of pixel values between the mutually adjacent frames.

Figure 20:
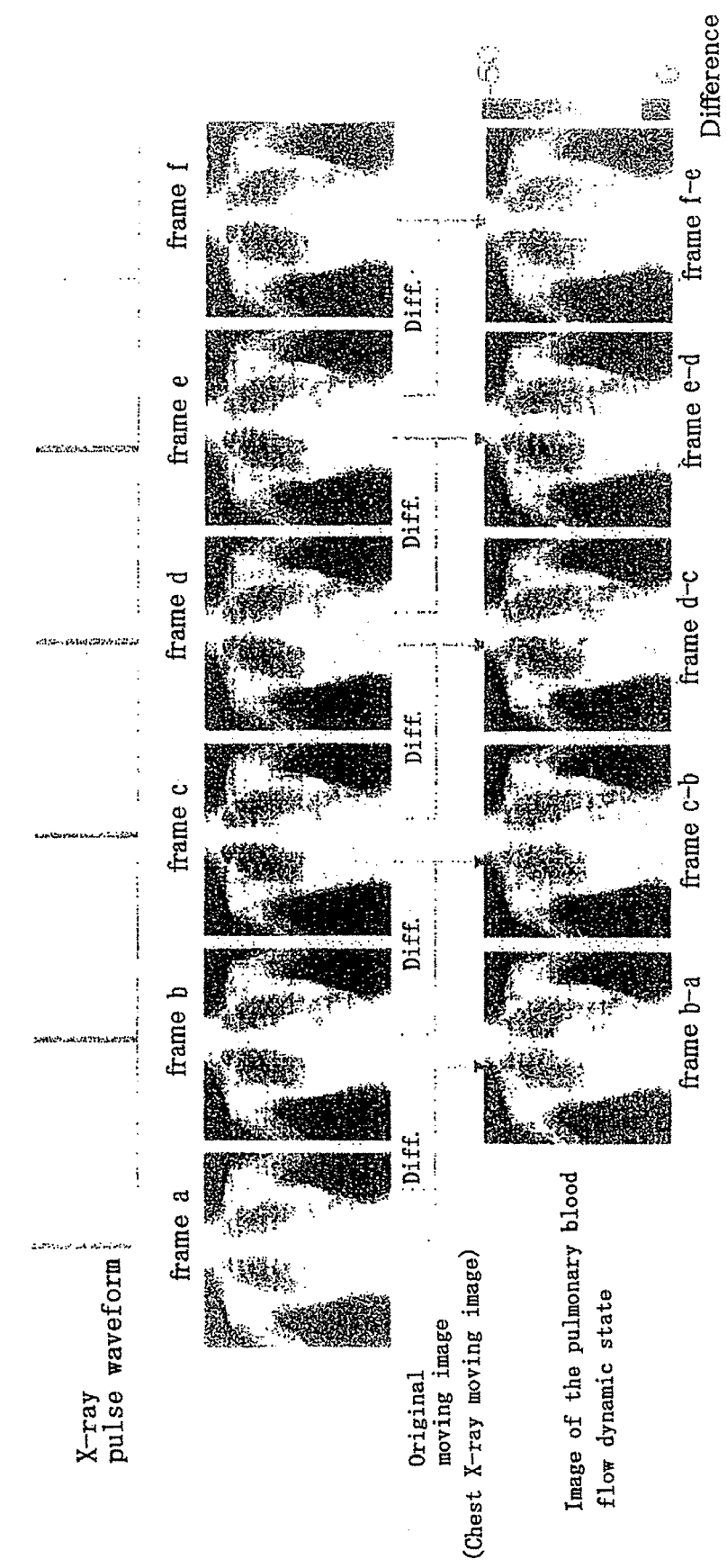
FIG. 20 is another computer algorithm for producing images of a pulmonary blood flow dynamic state with the pulmonary blood flow dynamic state analyzing means 43.

FIG. 20 is another computer algorithm for producing images of a pulmonary blood flow dynamic state with the pulmonary blood flow dynamic state analyzing means 43. In FIG. 20, the axis of abscissae in the graph represents a temporal axis. In a descending order from the top, the electrocardiogram, the X-ray pulse waveform, the chest X-ray moving images, the images of the pulmonary blood flow dynamic state in which the difference of the pixel values is indicated in color in contrasting density are displayed. The images of the pulmonary blood flow dynamic state are prepared respectively based on the difference of the pixel values between the adjacent frames a and b, frames b and c, frames c and d, frames d and e and frames e and f. Since the periods during the cardiac chamber systolic and diastolic phases can be grasped by the electrocardiogram as illustrated in FIG. 15, the pixel variation, that is, the level of increase and decrease of the pulmonary blood flow, of the image of the pulmonary blood flow dynamic state for each time can be recognized on the basis of pixel unit.

In the continuous X-ray image screening examination device 1 illustrated in FIG. 1 and FIG. 2, the pulmonary blood flow dynamic state analyzing means 43 of the control part 30 can prepare an image of the pulmonary blood flow dynamic state based on the difference between the average value of the pixel values for one heart beat calculated for each pixel and the pixel value of another frame for one heart beat calculated for each pixel. The cardiac blood flow dynamic state analyzing means is likewise.

FIG. 21 illustrates another computer algorithm for producing images of a pulmonary blood flow dynamic state with the pulmonary blood flow dynamic state analyzing means 43. In FIG. 21, the axis of abscissae in the graph represents the temporal axis. In a descending order from the top, the electrocardiogram, the X-ray pulse waveform, variation of pixel value in a certain one pixel are displayed. The pulmonary blood flow dynamic state analyzing means 43 extracts the maximum value and the minimum value of the pixel values for each pixel to calculate the average value from the maximum value and the minimum value. The difference between that average value and the pixel values of the other frames is calculated. With the difference, the images of the pulmonary blood flow dynamic state are prepared. Such processing is carried out on the basis of heart beat.

Here, as illustrated in FIG. 1, the continuous X-ray image screening examination device 1 is configured by a computer comprising a CPU 10, a volatile storage medium such as a RAM 13, a nonvolatile storage medium such as a ROM 12, a mouse 18 as well as a keyboard 19, an input apparatus such as a pointing device, an indicator 17 displaying images and data, an outside X-ray detector 2, interfaces I/F 14 and 15 for communication with the X-ray generator 3 and the electrocardiogram recording apparatus 5. The respective functions of the control part 30 and the analysis part 40 which the continuous X-ray image screening examination device 1 comprises are respectively realized by causing the CPU 10 to execute programs in which those functions are described. In addition, those programs can be distributed by being stored in a storage medium such as magnetic disk (floppy disk, hard disk HD 11 and the like), optical disk (CD-ROM, DVD and the like) and semiconductor memory.

In addition, such a continuous X-ray image screening examination device 1 is used in fields such as screening examinations such as health examination, follow-up examinations for heart disease patients and alternative examination for detailed examination in nuclear medicine examinations and the like. In addition, installation in a medical clinic at an airport is possible for examinations on economy-class syndrome.

The invention claimed is:

1. A continuous X-ray image screening examination device to which an X-ray moving image of an examinee is input and which generates information for assessing blood flow with the X-ray moving image, wherein the X-ray moving image is generated without a contrast agent characterized by comprising an image store configured to store a plurality of frames configuring the X-ray moving image and an analysis part configured to read a frame from the image store, to calculate a pixel value increased and decreased by blood flow amount of only blood within a predetermined range for each of the read frames and to generate temporal variation of the calculated pixel value reflecting a heart beat variation as blood flow information.

2. The continuous X-ray image screening examination device according to claim 1, characterized in that the analysis part reads the frame from the image store to generate blood flow information on temporal relation to a heart beat phase based on the read frame.

3. The continuous X-ray image screening examination device according to claim 1 further comprising an electrocardiogram store configured to store an electrocardiogram of the examinee, characterized in that the analysis part reads the frame from the image store and the electrocardiogram from the electrocardiogram store respectively to generate blood flow information on temporal relation to the electrocardiogram based on the read frame.

4. The continuous X-ray image screening examination device according to claim 3, characterized in that the analysis part has local pulmonary blood flow analyzing means for reading the plurality of frames from the image store and an electrocardiogram from the electrocardiogram store respectively, for calculating an average pixel value of any region among a lung field region, a lung field region subjected to dividing and a region of interest designated by an operator for each of the read frame and for generating an average pixel value for each of the regions and the read electrocardiogram as chronologically synchronized information.

5. The continuous X-ray image screening examination device according to claim 3, characterized in that the analysis part has local cardiac blood flow analyzing means for reading a plurality of frames from the image store and an electrocardiogram from the electrocardiogram store respectively and for calculating an average pixel value of a predetermined region inside a mediastinal part for each of the read frames.

6. The continuous X-ray image screening examination device according to claim 4, characterized in that the local pulmonary blood flow analyzing means further recognizes one heart beat from the electrocardiogram, calculates a rate of change of pixel from the average pixel value of each frame for one heart beat and compares the calculated rate of change of pixel for each of the regions.

7. The continuous X-ray image screening examination device according to claim 4, characterized in that the local pulmonary blood flow analyzing means further calculates at least one among a delay time from a first time point when an R wave occurs in the electrocardiogram until a second time point corresponding to a minimum value of an average pixel value, an angle of rising at and after the second time point of the minimum value of the average pixel value and the difference between the maximum value and the minimum value of the average pixel value.

8. The continuous X-ray image screening examination device according to claim 4, characterized in that the analysis part further has heart wall movement analyzing means for detecting a boundary site between the lung field region and the heart based on the pixel value for each frame to calculate quantity of variation of the boundary site as heart wall movement.

9. The continuous X-ray image screening examination device according to claim 4, characterized in that the analysis part further has pulmonary blood flow dynamic state analyzing means for reading the plurality of frames from the image store and the electrocardiogram from the electrocardiogram store respectively, specifying, from the electrocardiogram, timing when an R wave occurs, specifying a frame corresponding to the R wave, calculating the difference between pixel values of the specified frame and another frame for one heart beat and generating an image of a pulmonary blood flow dynamic state with the difference of the pixel values.

10. The continuous X-ray image screening examination device according to claim 4, characterized in that the analysis part further has pulmonary blood flow dynamic state analyzing means for reading a plurality of frames from the image store and the electrocardiogram from the electrocardiogram store respectively, calculating the difference between pixel values of the temporarily adjacent frames and generating an image of pulmonary blood flow dynamic state with the difference of the pixel values.

11. The continuous X-ray image screening examination device according to claim 4, characterized in that the analysis part further has pulmonary blood flow dynamic state analyzing means for reading the plurality of frames from the image store and the electrocardiogram from the electrocardiogram store respectively, calculating an average value from the maximum value and the minimum value of pixel values of each frame for one heart beat for each pixel based on the electrocardiogram, calculating the difference between the pixel value and the calculated average value and generating an image of pulmonary blood flow dynamic state with the difference of the pixel values.

12. The continuous X-ray image screening examination device according to claim 4, characterized in that the analysis part further has pulmonary blood flow distribution analyzing means for reading a plurality of frames from the image store and the electrocardiogram from the electrocardiogram store respectively, specifying, from the electrocardiogram, timing when an R wave occurs, specifying a frame corresponding to the R wave, generating a Maximum Intensity Projection (MIP) image for one heart beat, calculating the difference between pixel values of the MIP image and the image of the specified frame and generating an image of pulmonary blood flow distribution with the difference of the pixel values.

13. The continuous X-ray image screening examination device according to claim 9, further comprising a pulse waveform store for storing an X-ray pulse waveform specifying timing for detecting X-rays, characterized in that the pulmonary blood flow dynamic state analyzing means reads an X-ray pulse waveform from the pulse waveform store to specify a frame corresponding to an R wave based on the X-ray pulse waveform.

14. The continuous X-ray image screening examination device according to claim 1, characterized in that the analysis part calculates a pixel value of a lung region of the read frame, determines a frame corresponding to an R wave in heart beat phase based on the pixel value and generates pulmonary blood information.

15. The continuous X-ray image screening examination device according to claim 1, characterized in that the analysis part calculates heart wall movement from the read frame, determines a frame corresponding to an R wave in heart beat phase based on the heart wall movement and generates pulmonary blood information.

16. The continuous X-ray image screening examination device according to claim 5, characterized in that the analysis part further has cardiac blood flow dynamic state analyzing means for reading the plurality of frames from the image store and the electrocardiogram from the electrocardiogram store respectively, for specifying, from the electrocardiogram, timing when an R wave occurs, for specifying a frame corresponding to the R wave, for calculating the difference between pixel values of the specified frame and another frame for one heart beat and for generating an image of cardiac blood flow dynamic state with the difference of the pixel values and cardiac blood flow distribution analyzing means for reading the plurality of frames from the image store and the electrocardiogram from the electrocardiogram store respectively, for specifying, from the electrocardiogram, timing when an R wave occurs, for specifying a frame corresponding to the R wave, for generating a Maximum Intensity Projection (MIP) image for one heart beat, for calculating the difference between pixel values of the MIP image and the image of the specified frame and generating an image of cardiac blood flow distribution with the difference of the pixel values, and characterized in that the local pulmonary blood flow analyzing means further recognizes one heart beat from the electrocardiogram, calculates a rate of change of pixel from the average pixel value of each frame for one heart beat and compares the calculated rate of change of pixel for each of the regions.

17. A continuous X-ray image screening examination program using an apparatus comprising an image store configured to store a plurality of frames, said plurality of frames configuring an X-ray moving image of an examinee, to generate information for assessing blood flow with the X-ray moving image, wherein the X-ray moving image is generated without a contrast agent, the program causing a computer configuring the apparatus to execute a process (1) for reading a frame from the image store, a process (2) for calculating a pixel value increased and decreased by blood flow amount of only blood within a predetermined range for each of the read frames and a process (3) for generating temporal variation of the calculated pixel value reflecting a heart beat variation as blood flow information.

18. A continuous X-ray image screening examination program using an apparatus comprising an image store configured to store a plurality of frames, said plurality of frames configuring an X-ray moving image of an examinee, to generate information for assessing blood flow with the X-ray moving image, wherein the X-ray moving image is generated without a contrast agent, the program causing a computer configuring the apparatus to execute a process (1) for reading a frame from the image store, a process (2) for assuming a heart beat phase based on the read frame and a process (3) for generating blood flow information from the assumed heart beat phase and the read frame.

19. The continuous X-ray image screening examination program according to claim 17, wherein the apparatus further comprises an electrocardiogram store configured to store an electrocardiogram of an examinee, and the program causes the computer to execute a process (4) for reading an electrocardiogram from the electrocardiogram store, a process (5) for assuming a heart beat phase based on the read electrocardiogram and a process (6) for generating blood flow information from the assumed heart beat phase and the read frame.

20. A recording medium recording the continuous X-ray image screening examination program according to claim 17.

* * * * *